US005472954A

United States Patent [19]
Loftsson

[11] Patent Number: 5,472,954
[45] Date of Patent: * Dec. 5, 1995

[54] CYCLODEXTRIN COMPLEXATION

[75] Inventor: Thorsteinn Loftsson, Reykjavik, Iceland

[73] Assignee: Cyclops h.f., Reykjavik, Iceland

[ * ] Notice: The portion of the term of this patent subsequent to Jun. 28, 2011, has been disclaimed.

[21] Appl. No.: 240,510

[22] Filed: May 11, 1994

Related U.S. Application Data

[63] Continuation-in-part of Ser. No. 912,853, Jul. 14, 1992, Pat. No. 5,324,718.

[30] Foreign Application Priority Data

Jul. 6, 1993 [EP] European Pat. Off. .............. 93305280

[51] Int. Cl.$^6$ ...................... A61K 47/48; A61K 31/735; C08B 37/16
[52] U.S. Cl. .................. 514/58; 514/772.2; 514/772.3; 514/772.6; 514/773; 514/777; 514/779; 514/781; 536/103
[58] Field of Search ................... 514/58, 772.2, 514/772.3, 772.6, 773, 777, 779, 781; 536/103

[56] References Cited

U.S. PATENT DOCUMENTS

| | | | |
|---|---|---|---|
| 3,459,731 | 8/1969 | Gramera et al. | 260/209 |
| 4,426,292 | 1/1984 | Wernick et al. | 210/635 |
| 4,596,795 | 6/1986 | Pitha | 514/58 |
| 4,727,064 | 2/1988 | Pitha | 514/58 |
| 4,834,985 | 5/1989 | Elger et al. | 424/488 |
| 4,883,785 | 11/1989 | Chow et al. | 514/58 |
| 4,983,586 | 1/1991 | Bodor | 514/58 |
| 5,002,935 | 3/1991 | Bodor | 514/58 |
| 5,017,566 | 5/1991 | Bodor | 514/58 |
| 5,024,998 | 6/1991 | Bodor | 514/58 |
| 5,070,081 | 12/1991 | Majid et al. | 536/103 |
| 5,120,546 | 6/1992 | Hansen et al. | 424/448 |
| 5,321,014 | 6/1994 | Janz et al. | 514/58 |
| 5,324,718 | 6/1994 | Loftsson | 514/58 |

FOREIGN PATENT DOCUMENTS

| | | |
|---|---|---|
| 0213514 | 3/1987 | European Pat. Off. . |
| 0327766 | 8/1989 | European Pat. Off. . |
| 0149197 | 3/1990 | European Pat. Off. . |
| 0472327 | 2/1992 | European Pat. Off. . |
| 0437478 | 4/1993 | European Pat. Off. . |
| 0579435 | 1/1994 | European Pat. Off. . |
| 466134 | 1/1992 | Sweden . |
| 91/04026 | 4/1991 | WIPO . |
| 92/03141 | 3/1992 | WIPO . |
| 92/09307 | 6/1992 | WIPO . |

OTHER PUBLICATIONS

Villiers, C. R. *Acad. Sci.*, 112, 536–538(1891).
Schardinger, *Z Unters. Nahr. Genussm.*, 6, 865–880(1903).
Szejtli, *Pharm. Techn. Int.*, 3(2), 15–22(1991).
Szejtli, *Pharm. Techn. Int.*, 16–24(1991).
Loftsson et al, *Pharm. Ztg. Wiss.*, 4/136:5–10(1991).
Hirayama et al, in *Cyclodextrins and their industrial uses*, ed. D. Duchêne, Editions de Santé, Paris, 1987, pp. 133–172.
Hassan et al, *Int. J. Pharm.* 58, 19–24(1990).
Nakai et al, *Chem. Pharm. Bull*, 35(11), 4609–4615(1987).
Nakai et al, *Chem. Pharm. Bull*, 37(4), 1055–1058(1989).
Nakai et al, *Chem. Pharm. Bull*, 38(3), 728–732(1990).
Nakai et al, *Chem. Pharm. Bull.*, 38(5), 1345–1348(1990).
Nakai et al, *Chem. Pharm. Bull.*, 39(6), 1532–1535(1991).
Schmidt et al, *Starch/Stärke*, 39(6), 203–207 (1987).
Loftsson et al, *Acta. Pharm. Nord*, 1(4), 185–193(1989).
*Remington's Pharmaceutical Sciences*, 18th edition, Alfonso R. Gennaro (ed.), Mack Publishing Co., Easton, Pa., 1990, pp. 291–294.
Martin et al, *Physical Pharmacy*, 3rd edition, Lea & Febinger, Philadelphia, Pa. 1983, pp. 592–638.
Florence et al, *Physiochemical Principles of Pharmacy*, 2nd edition, MacMillan Press, London, 1988, pp. 281–334.
Leung et al, in *Controlled Drug Delivery*, 2nd edition, Robinson and Lee, editors, Marcel Dekker, Inc., New York, 1987, pp. 433–480.
Uekama et al, *Journal of Inclusion Phenomena*, 1, 309–312(1984).
Pagington, J. S., "β–cyclodextrin: the success of molecular inclusion," in *Chemistry in Britain*, May 1987, 455–458.
Loftsson et al, *Eur. J. Pharm. Biopharm.*, vol. 37, No. 1, Mar. 1991, 30–33.
STN FILE SUPPLIER & FILE MEDLINE AN=92324215 (Orienti et al).
*Chemical Abstracts*, vol. 107, No. 16, 1987, abstract No. 140916f.
DATABASE WPI, Week 9037, Derwent Pulication Ltd., London, GB, AN 90–279330.
*THE MERCK INDEX*, eleventh edition, ed. Susan Budavari et al, Merck & Co., Inc. Rahway, N.J., 1989, pp. 959, 1248 and 1467.

(List continued on next page.)

*Primary Examiner*—Ronald W. Griffin
*Attorney, Agent, or Firm*—Burns, Doane, Swecker & Mathis

[57] ABSTRACT

The invention provides a method for enhancing the complexation of a cyclodextrin with a lipophilic and/or water-labile active ingredient which is a drug, cosmetic additive, food additive or agrochemical, comprising combining from about 0.1 to about 70% (weight/volume) of a cyclodextrin, from about 0.001 to about 5% (weight/volume) of a pharmacologically inactive water-soluble polymer acceptable for use in a pharmaceutical, cosmetic, food or agricultural composition, and said lipophilic and/or water-labile active ingredient in an aqueous medium, the polymer and cyclodextrin being dissolved in the aqueous medium before the active ingredient is added, the aqueous medium which comprises the polymer and cyclodextrin being maintained at from about 30° to 150° C. for a period of from about 0.1 to about 100 hours before, during and/or after the active ingredient is added, optionally followed by removal of water. Related methods, co-complexes of active ingredient/cyclodextrin/polymer, pharmaceutical, cosmetic, food and agricultural compositions and cyclodextrin/polymer complexing agents are also provided.

119 Claims, 5 Drawing Sheets

OTHER PUBLICATIONS

*COSMETIC AND DRUG PRESERVATION:* PRINCIPLES AND PRACTICE, ed. Jon J. Kabara, Marcel Dekker, Inc., New York, N.Y., 1984, pp. 71–72.

*THE UNITED STATES PHARMACOPEIA, USP XXII,* twenty–second revision, Jan. 1, 1990, U.S. Pharmacopeial Convention, Inc. Rockville, Md., p. 8.

Loftsson et al, *European Journal of Pharmaceutical Sciences,* 1(1994), 175–180.

Loftsson et al, *International Journal of Pharmaceutics,* 104(1994), 181–184.

Loftsson et al, "Topical acetazolamide–HPβCD eye drop solution," in Final Program and Abstracts for the 7th International Cyclodextrins Symposium, Tokyo, Japan, Apr. 25–28, 1994, p. 112, abstract P–B–25.

Loftsson et al, "Dexamethasone 2-hydroxypropyl–β–cyclodextrin eye drops," In Final Program and Abstracts for the 7th International Cyclodextrins Symposium, Tokyo, Japan, Apr. 25–28, 1994, p. 113, abstract P–B–26.

Loftsson et al, "The Effect of Polymers on Cyclodextrin Complexation," in Final Program and Abstracts for the 7th International Cyclodextrins Symposium, Tokyo, Japan, Apr. 25–28, 1994, p. 114, abstract P–B–27.

Stefánsson et al, "Dexamethasone 2-Hydroxypropyl–β–cyclodextrin (HPβCD) Eye Drops," in *Investigative Ophthalmology & Visual Science,* Annual Meeting Abstract Issue, Mar. 15, 1994, vol. 35, No. 4, p. 2217, abstract 4459–11.

Thórisdóttir et al, "Topical Acetazolamide in 2-Hydroxypropyl–β–Cyclodextrin (HPβCD) Eye Drops Lowers Intraocular Pressure in Humans," in *Investigative Ophthalmology & Visual Science,* Annual Meeting Abstract Issue, Mar. 15, 1994, vol. 35, No. 4, p. 2220, abstract 4479–4531.

Florence et al, *Physiochemical Principles of Pharmacy,* 2nd ed., Macmillan Press, London 1988, pp. 24, 297–298.

Higuchi, *J. Soc. Cosm. Chem.,* 11, 85–97(1960).

Loftsson, *Arch. Pharm. Chem., Sci. Ed.,* 10, 17–24(1981).

Chien, *Novel Drug Delivery Systems,* 2nd Ed., Marcel Dekker, New York 1992, pp. 171–173.

Peppas et al, "Surface, interfacial and molecular aspects of polymer bioadhesion on soft tissues," in J. M. Anderson and S. W. Kim (editors), *Advances in Drug Delivery Systems,* Elsevier, Amsterdam 1986, pp. 257–275.

Attwood et al: *Surfactant Systems. Their Chemistry, Pharmacy and Biology,* Chapman and Hall, London, 1983, pp. 361–365.

Myers, *Surfactant Science and Technology,* VCH Publishers, New York, 1988, pp. 142–145.

CYCLODEXTRIN COMPLEXATION

CROSS-REFERENCE TO RELATED APPLICATION

This is a continuation-in-part of applicant's U.S. patent application Ser. No. 07/912,853, filed Jul. 14, 1992, now U.S. Pat. No. 5,324,718, incorporated by reference herein in its entirety and relied upon.

FIELD OF THE INVENTION

The present invention relates to the use of certain polymers in the preparation of cyclodextrin-drug complexes as a means for increasing the solubilizing and stabilizing effects of cyclodextrin derivatives on drugs, and complexation therewith. Pharmaceutical compositions comprising complexes prepared according to these methods are characterized by fast and efficient drug release. The invention further relates to polymer/cyclodextrin complexing agents. Still further, the invention relates to use of the polymers to increase the solubilizing and stabilizing effects of cyclodextrins on food additives, agrochemicals and chemicals used in cosmetics, and complexation therewith.

BACKGROUND OF THE INVENTION

Formulation of pharmaceutical dosage forms is frequently hampered by the poor aqueous solubility and stability of the drugs, which in turn can severely limit their therapeutic application. Also, the slow dissolution of solid state drug formulations and the side-effects of some drugs result from their poor aqueous solubility. Drug degradation products, formed in the pharmaceutical dosage forms, can also result in severe side-effects. Increasing drug solubility and stability through appropriate formulation can, thus, lead to increased therapeutic efficiency of the drug. Various methods have been used to increase the solubility and stability of drugs, such as the use of organic solvents, emulsions, liposomes and micelles, adjustments of pH and the dielectric constant of the solvent system, chemical modifications, and complexation of the drugs with appropriate complexing agents, e.g., cyclodextrins. Similar approaches have been taken to increase the solubility and stability of food additives, agrochemicals and cosmetic additives.

Cyclodextrins were first isolated by Villiers in 1891 as a digest of *Bacillus amylobacter* on potato starch [see A. Villiers: Sur la fermentation de la fécule par l'action du ferment butyriqué. *C.R. Acad. Sci.*, 112, 536–538 (1891)], but the foundations of cyclodextrin chemistry were laid down by Schardinger in the period 1903–1911 [see, for example, F. Schardinger: Über thermophile Bacterien aus verschiedenen Speisen und Milch, sowie über einige Umsetzungsproducte darselben in kohlenhydrathaltigen Nährlösungen, darunter krystallisierte Polysaccharide (Dextrine) aus Stärke, *Z. Unters. Nahr. Genußm.*, 6, 865–880 (1903)] and much of the older literature refers to cyclodextrins as Schardinger's dextrins. Until 1970, only small amounts of cyclodextrins could be produced in the laboratory and the high production cost prevented the usage of cyclodextrins in industry. In recent years, dramatic improvements in cyclodextrin production and purification have been achieved and the cyclodextrins have become much cheaper. This has made industrial application of cyclodextrins possible.

Cyclodextrins are cyclic oligosaccharides with hydroxyl groups on the outer surface and a void cavity in the center. Their outer surface is hydrophilic, and therefore they are usually soluble in water, but the cavity has a lipophilic character. The most common cyclodextrins are α-cyclodextrin, β-cyclodextrin and γ-cyclodextrin, consisting of 6, 7 and 8 α-1,4-linked glucose units, respectively. The number of these units determines the size of the cavity.

Cyclodextrins are capable of forming inclusion complexes with a wide variety of hydrophobic molecules by taking up a whole molecule, or some part of it, into the cavity. The stability of the complex formed depends on how well the guest molecule fits into the cyclodextrin cavity. Common cyclodextrin derivatives are formed by alkylation (e.g., methyl- and ethyl-β-cyclodextrin) or hydroxyalkylation of the hydroxyl groups (e.g., hydroxypropyl- and hydroxyethyl-derivatives of α-, β-, and γ-cyclodextrin) or by substituting the primary hydroxyl groups with saccharities (e.g., glucosyl- and maltosyl-β-cyclodextrin). Hydroxypropyl-β-cyclodextrin and its preparation by propylene oxide addition to β-cyclodextrin, and hydroxyethyl-β-cyclodextrin and its preparation by ethylene oxide addition to β-cyclodextrin, were described in a patent of Gramera et al. (U.S. Pat. No. 3,459,731, issued August 1969) over 20 years ago. For a comprehensive review of cyclodextrins see *Cyclodextrins and their industrial uses*, editor Dominique Duchêne, Editions de Santé, Paris, 1987. For a more recent overview, see J. Szejtli: Cyclodextrins in drug formulations: Part 1, *Pharm. Techn. Int.* 3(2), 15–22 (1991); and J. Szejtli: Cyclodextrins in drug formulations: Part II, *Pharm. Techn. Int.* 3(3), 16–24 (1991).

Numerous reports have been published with respect to the solubilizing effects of cyclodextrins. The general procedure described in these reports for preparing aqueous cyclodextrin solutions containing various drugs is as follows: An excess amount of the drug is added to an aqueous cyclodextrin solution and the suspension formed is agitated for up to one week at room temperature. Then the suspension is filtered or centrifuged to form a clear drug-cyclodextrin complex solution. For the preparation of solid formulations of the drug-cyclodextrin complex, the water is removed from the aqueous drug-cyclodextrin complex solution by evaporation in a rotation evaporator, in a spray dryer or by lyophilization. Pitha (Josef Pitha: Administration of sex hormones in the form of hydrophilic cyclodextrin derivatives, U.S. Pat. No. 4,596,795, issued Jun. 24, 1986) describes inclusion complexes of sex hormones, particularly testosterone, progesterone, and estradiol, with specific cyclodextrins, preferably hydroxypropyl-β-cyclodextrin and poly-β-cyclodextrin. The complexes enable the sex hormones to be successfully delivered to the systemic circulation via the sublingual or buccal route. In another patent (Josef Pitha: Pharmaceutical preparations containing cyclodextrin derivatives, U.S. Pat. No. 4,727,064, issued Feb. 23, 1988) Pitha describes formulations of a number of drugs with various cyclodextrin derivatives, mainly hydroxypropyl-β-cyclodextrin but also hydroxypropyl-γ-cyclodextrin. In a series of patents (N. S. Bodor: Improvements in redox systems for brain-targeted drug delivery, U.S. Pat. No. 5,002,935, issued Mar. 26, 1991; N. S. Bodor: Pharmaceutical formulations for parenteral use, U.S. Pat. No. 4,983,586, issued Jan. 8, 1991; N. S. Bodor: Redox systems for brain-targeted drug delivery, U.S. Pat. No. 5,017,566, issued May 21, 1991; and N. S. Bodor: Pharmaceutical formulations for parenteral use, U.S. Pat. No. 5,024,998, issued Jun. 18, 1991), Bodor describes formulations of a number of drugs with hydroxypropyl, hydroxyethyl, glucosyl, maltosyl and maltotriosyl derivatives of β- and γ-cyclodextrin. Also, Brauns and Müller (U. Brauns and B. W. W. Müller: Pharmazeutische Präparate yon in Wasser schwerlöslichen oder instabilen Arznelstoffen und Verfahren zu Ihrer Herstellung, European Patent No.: 0 149 197 B1 dated Mar. 21, 1990) have described formulations of drugs with various β-cyclodextrin derivatives, mainly hydroxypropyl-β-cyclodextrin. The solubilizing and stabilizing effects of hydroxypropyl-β-cyclodextrin on drugs have been reviewed by T. Loftsson, M. E. Brewster, H. Derendorf and N. Bodor: 2-Hydroxypropyl-β -cyclodextrin: Properties and usage in pharmaceutical formulations. *Pharm. Ztg. Wiss.* 4/136:5–10 (1991).

Methods of preparing drug-cyclodextrin complexes have been described by Hirayama and Uekama IF. Hirayama and K. Uekama: Methods of investigating and preparing inclusion compounds. In: D. Duchêne (editor), Cyclodextrins and their industrial uses. Editions de Santé, Paris, 1987, pp. 133–172]. In solution, the drug-cyclodextrin complexes are prepared by the simple method described above and the complexation evaluated by determination of stability constants by a solubility method, a kinetic method, a spectroscopic method or some other analytical method. On a laboratory scale, solid drug-cyclodextrin complexes are usually formed by lyophilization of drug-cyclodextrin complex solution, but on an industrial scale, other methods are also used such as the kneading method, spray-drying, coprecipitation, neutralization and grinding methods. In none of these methods are water-soluble pharmaceutical polymers, or other polymers in general, used for enhancing the drug-cyclodextrin complexation.

There are few samples of formation of drug-cyclodextrin complexes by heating. Thus, Hassan et al., Int. J. Pharm. 58, 19–24 (1990), prepared a famotidine-β-cyclodextrin complex by adding the drug to aqueous β-cyclodextrin solution, heating the mixture under reflux for 1 hour and then stirring it at room temperature for 5 days. The solution which formed was concentrated by evaporation under vacuum and the precipitate which formed was filtered and dried under vacuum at 50° C. In a series of articles, Nakai et al. describe how they make cyclodextrin inclusion complexes by heating ground mixtures of physical mixtures to 60° to 130° C. in sealed containers. See Nakai et al., *Chem. Pharm. Bull.* 35(11),4609–4615 (1987); Nakai et al., *Chem. Pharm. Bull.* 37(4), 1055–1058 (1989); Nakai et al., *Chem. Pharm. Bull.* 38(3), 728–732 (1990); Nakai et al., *Chem. Pharm. Bull.* 38(5), 1345– 1348 (1990); and Nakai et al., *Chem. Pharm. Bull.* 39(6), 1532–1535 (1991). Finally, Schmidt and Maier [E. Schmidt and H. G. Maier: Thermostabile Bindung yon Aromastoffen an Stärke. Teil 2: Bindung yon Menthol durch Autoklavieren, Starch/Stärke, 39(6), 203–207 (1987)] describe formation of thermostable binding of menthol to various types of starches, including β-cyclodextrin, by autoclaving. In none of the above mentioned articles are starches, or other polymers, used to enhance complexation of drugs by cyclodextrins.

Due to the negative enthalpy of cyclodextrin complexation, the solubility enhancement of drugs by aqueous cyclodextrin solutions is generally larger at low temperature than at high temperature [T. Loftsson and N. Bodor: Effects of 2-hydroxypropyl-β-cyclodextrin on the aqueous solubility of drugs and transdermal delivery of 17β-estradiol, *Acta Pharm. Nord.*, 1(4), 185–193 (1989)]. Also, additives such as sodium chloride, buffer salts, surfactants and organic solvents (e.g., ethanol) usually reduce the solubilizing effects of cyclodextrins.

SUMMARY AND OBJECTS OF THE INVENTION

One object of the present invention is to provide a method for enhancing the complexation of cyclodextrins with lipophilic and/or water-labile drugs, food additives, cosmetic additives and agrochemicals.

Another object of the invention is to provide a method for increasing the solubilizing and stabilizing effects of cyclodextrins on drugs which are insoluble or sparingly soluble or unstable in water, and on food additives, cosmetic additives and agrochemicals which are insoluble or sparingly soluble or unstable in water.

Another object of the invention is to provide novel co-complexes of drugs, cyclodextrins and selected polymers, and of food additives, cosmetic additives and agrochemicals, with cyclodextrins and selected polymers.

Yet another object of the invention is to provide pharmaceutical compositions comprising novel drug complexes, as well as analogous food, cosmetic and agricultural compositions.

Still another object of the invention is to provide a novel complexing agent for use in solubilizing and/or stabilizing a lipophilic and/or water-labile drug, food additive, cosmetic additive or agrochemical.

In accord with these and other objects, the present invention provides the following:

(1) A method for enhancing the complexation of a cyclodextrin with a lipophilic and/or water-labile active ingredient which is a drug, cosmetic additive, food additive or agrochemical, comprising combining from about 0.1 to about 70% (weight/volume) of cyclodextrin and from about 0.001 to about 5% (weight/volume), preferably from about 0.01 to about 0.5% (weight/volume), of a pharmacologically inactive water-soluble polymer acceptable for use in a pharmaceutical, cosmetic, food or agricultural composition, with a lipophilic and/or water-labile active ingredient in an aqueous medium to form a complex, the polymer and cyclodextrin being dissolved in the aqueous medium before the active ingredient is added, and the aqueous medium which comprises the polymer and cyclodextrin being maintained at from about 30° to about 150° C. for a period of from about 0.1 to about 100 hours before, during and/or after the active ingredient is added, optionally followed by removal of water;

(2) A method for solubil izing and/or stabilizing a lipophilic and/or water-labile active ingredient which is a drug, cosmetic additive, food additive or agrochemical in an aqueous medium, comprising complexing the active ingredient in an aqueous medium with from about 0.1 to about 70% (weight/volume) of cyclodextrin and from about 0.001 to about 5% (weight/volume), preferably from about 0.01 to about 0.5% (weight/volume), of a pharmacologically inactive water-soluble polymer acceptable for use in a pharmaceutical, cosmetic, food or agricultural composition, the polymer and cyclodextrin being dissolved in the aqueous medium before the active ingredient is added, the aqueous medium which comprises the polymer and cyclodextrin being maintained at from about 30 to about 150° C. for a period of from about 0.1 to about 100 hours before, during and/or after the active ingredient is added;

(3) A co-complex of a lipophilic and/or water-labile active ingredient which is a drug, cosmetic additive, food additive or agrochemical with a cyclodextrin and a pharmacologically inactive water-soluble polymer acceptable for use in a pharmaceutical, cosmetic, food or agricultural composition, the ratio by weight of cyclodextrin to polymer being from about 4:1 to about 50,000:1, preferably from about 4:1 to 10,000:1, most preferably from about 100:1 to about 1,000:1; the molecular ratio of active ingredient to cyclodextrin being from about 0.33 to about 3.0 molecules of active ingredient per molecule of cyclodextrin in the co-complex;

(4) A composition comprising:

(a) a complex prepared by complexing a lipophilic and/or water-labile active ingredient which is a drug, cosmetic additive, food additive or agrochemical in an aqueous medium comprising from about 0.1 to about 70% (weight/volume) of cyclodextrin and from about 0.001 to about 5% (weight/volume), preferably from about 0.01 to about 0.5% weight/volume, of a pharmacologically inactive water-soluble polymer acceptable for use in a pharmaceutical, cosmetic, food or agricultural composition, the polymer and cyclodextrin being dissolved in the aqueous medium before the active ingredient is added, the aqueous medium which comprises the polymer and cyclodextrin being maintained at from about 30 to about 150° C. for a period of from about 0.1 to about 100 hours before, during and/or after the drug is added, optionally followed by removal of water; and (b) a non-toxic carrier therefor acceptable for use in a pharmaceutical, cosmetic, food or agricultural composition;

(5) A composition comprising:

(a) a co-complex of a lipophilic and/or water-labile active ingredient which is a drug, cosmetic additive, food additive or agrochemical with a cyclodextrin and a pharmacologically inactive water-soluble polymer acceptable for use in a pharmaceutical, cosmetic, food or agricultural composition, the ratio by weight of cyclodextrin to polymer being from about 4:1 to about 50,000:1; preferably from about 4:1 to 10,000:1, most preferably from about 100:1 to about 1,000:1, the molecular ratio of active ingredient to cyclodextrin being from about 0.33 to about 3.0 molecules of active ingredient per molecule of cyclodextrin in the co-complex; and (b) a non-toxic carrier therefor acceptable for use in a pharmaceutical, cosmetic, food or agricultural composition; and (6) A complexing agent for use in solubilizing and/or stabilizing a lipophilic and/or water-labile active ingredient which is a drug, cosmetic additive, food additive or agrochemical, comprising a cyclodextrin and a pharmacologically inactive water-soluble polymer acceptable for use in a pharmaceutical, cosmetic, food or agricultural composition, the ratio by weight of cyclodextrin to polymer being from about 4:1 to about 50,000:1, preferably from about 4:1 to about 10,000:1, most preferably from about 100:1 to about 1,000: 1, said complexing agent being formed by heating the cyclodextrin and polymer in an aqueous medium at from about 30° to about 150° C. for a period of from about 0.1 to about 100 hours.

BRIEF DESCRIPTION OF THE DRAWINGS

Other objects and advantages of the present invention will be apparent from the following detailed description and accompanying drawings, in which.

DETAILED DESCRIPTION OF THE INVENTION AND PREFERRED EMBODIMENTS

Figure 1:
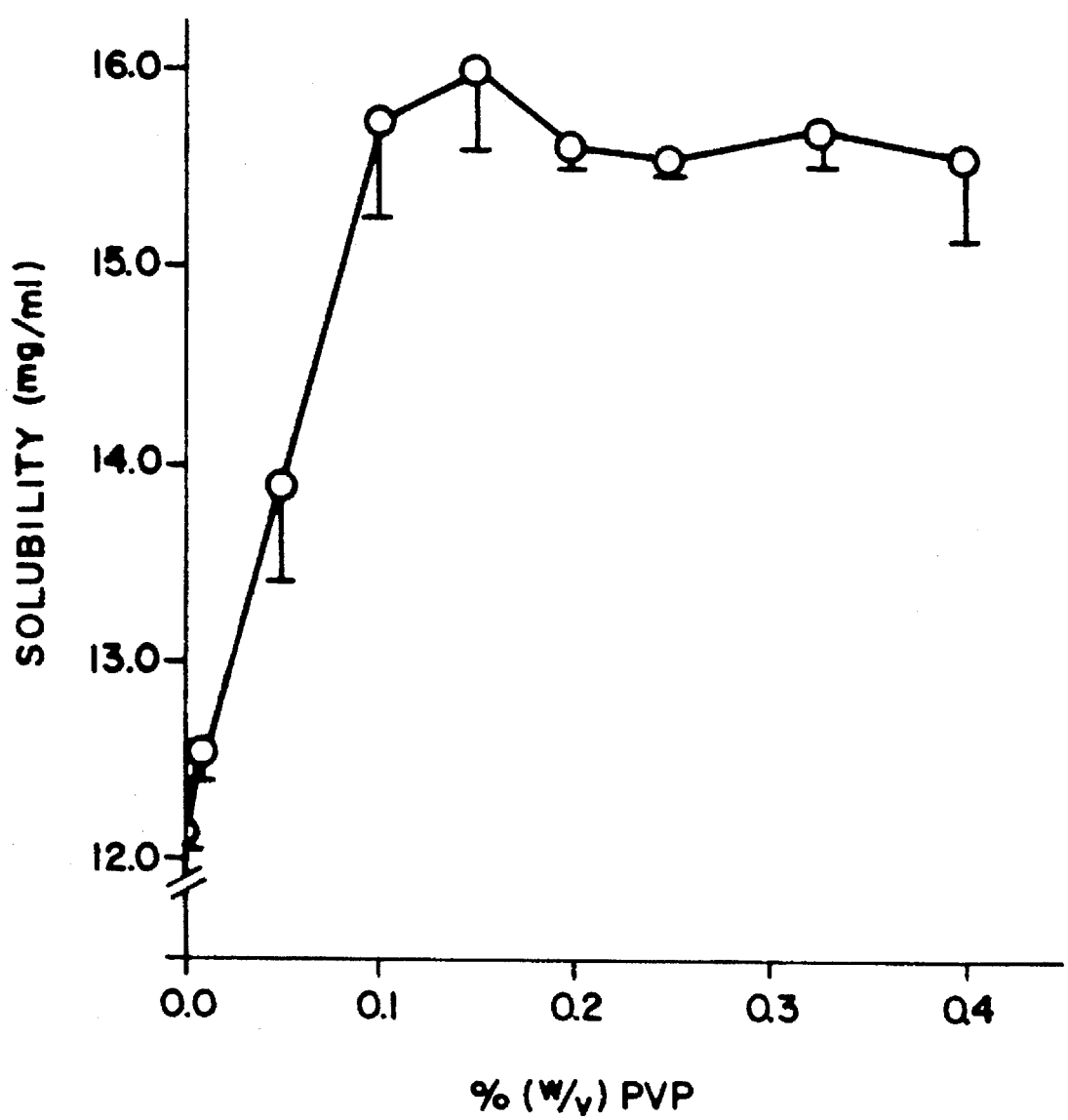
FIG. 1 is a plot of the solubilization of hydrocortisone, in mg/ml, in aqueous 10% HPβCD (2-hydroxypropyl-β-cyclodextrin) MS 0.6 solution containing varying amounts of PVP (polyvinylpyrrolidone)

Here and throughout this description, the following definitions are applicable:

The term "lipophilic" is used herein to describe drugs (or food additives or cosmetic additives or agrochemicals) which are lipid-soluble and hydrophobic, i.e., which are insoluble or sparingly soluble in water.

The term "water-labile" is used herein to describe drugs (or food additives or cosmetic additives or agrochemicals) which are unstable in water.

Cyclodextrins for use in the present invention include the natural cyclodextrins and their derivatives, including the alkylated and hydroxyalkylated derivatives and the branched cyclodextrins. Cyclodextrins and their derivatives which have been previously described as useful for complexation with drugs are of particular interest herein. In addition to α-, β-, and γ-cyclodextrins, the ether and mixed ether derivatives and those derivatives bearing sugar residues are of special interest. Especially useful herein are the hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α-, β- and γ-cyclodextrin; the maltosyl, glucosyl and maltotriosyl derivatives of α, β- and γ-cyclodextrin, which may contain one or more sugar residues, e.g., glucosyl or diglucosyl, maltosyl or dimaltosyl, as well as various mixtures thereof, e.g., a mixture of maltosyl and dimaltosyl derivatives; and the variously substituted alkylsulfonate-β-cyclodextrins, particularly when the alkyl group is of moderate length such as $C_4$–$C_8$. Specific cyclodextrin derivatives for use herein include hydroxypropyl-β -cyclodextrin, hydroxyethyl-β-cyclodextrin, hydroxypropyl-γ -cyclodextrin, hydroxyethyl-γ-cyclodextrin, dihydroxypropyl-β-cyclodextrin, glucosyl-α-cyclodextrin, glucosyl-β-cyclodextrin, diglucosyl-γ-cyclodextrin, maltosyl-α-cyclodextrin, maltosyl-β-cyclodextrin, maltosyl-7-cyclodextrin, maltotriosyl-β-cyclodextrin, maltotriosyl-γ-cyclodextrin and dimaltosylt-β -cyclodextrin, and mixtures thereof such as maltosyl-β -cyclodextrin/dimaltosyl-β-cyclodextrin, as well as methyl-β-cyclodextrin, and the sulfobutyl ether and sulfoheptyl ether derivatives of β-cyclodextrin (developed by CyDex, Kansas City, Kans.). Procedures for preparing the various cyclodextrin derivatives named above are well-known, for example, from Bodor U.S. Pat. No. 5,024,998 dated Jun. 18, 1991, and references cited therein. Particularly preferred cyclodextrins for use in the present invention are γ-cyclodextrin, α-cyclodextrin, β-cyclodextrin, and the hydroxypropyl, hydroxyethyl, dihydroxypropyl, glucosyl and maltosyl derivatives of α-, β- and γ-cyclodextrin, and their mixtures, especially those having a molar degree of substitution of from about 0.05 to about 10. The expression "molar degree of substitution" is used in the same sense as employed in Brauns and Müller European Patent No. 0149197 B1.

Suitable polymers for use herein are those which are soluble in water, are acceptable for use in pharmaceuticals and are pharmacologically inactive. Such polymers are well-known excipients commonly used in the field of pharmaceutical formulations. [See, for example, *Remington's Pharmaceutical Sciences,* 18th edition, Alfonso R. Gennaro (editor), Mack Publishing Company, Easton, Pa., 1990, pp. 291–294; Alfred Martin, James Swarbrick and Arthur Commaram, *Physical Pharmacy. Physical Chemical Principles in Pharmaceutical Sciences,* 3rd edition, Lea & Febinger, Philadelphia, Pa., 1983, pp. 592–638; A. T. Florence and D. Altwood, *Physicochemical Principles of Pharmacy,* 2nd edition, MacMillan Press, London, 1988, pp. 281–334.] Suitable polymers include water-soluble natural polymers, water-soluble semi-synthetic polymers (such as the water-soluble derivatives of cellulose) and water-soluble synthetic polymers. The natural polymers include polysaccharides such as inulin, pectins, algin derivatives (e.g., sodium alginate) and agar, and polypeptides such as casein and gelatin. The semisynthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g., carbomer). Other natural, semi-synthetic and synthetic polymers not named here which meet the criteria of water solubility, pharmaceutical acceptability and pharmacological inactivity are likewise considered to be within the arebit of the present invention. Particularly preferred polymers for use herein are sodium carboxymethylcellulose, hydroxypropyl methylcellulose and polyvinylpyrrolidone.

Water-soluble polymers for use with drugs herein, as pointed out above, need to be pharmaceutically acceptable and pharmacologically inactive. Generally speaking, such water-soluble polymers will also be acceptable for use with food additives, cosmetic additives and agrochemicals (agricultural chemicals), since the most stringent requirements are usually placed on pharmaceuticals, particularly for parenteral use. Conversely, however, a polymer which is not pharmaceutically acceptable could, for example, nevertheless be agriculturally acceptable, particularly for non-crop applications; such a polymer is intended for use herein in compositions with those non-drug materials, e.g., agrochemicals, which do not require pharmaceutical acceptability. Similarly, the water-soluble polymers for use with food and cosmetic additives need only be acceptable for use in foods and cosmetics.

As lipophilic and/or water-labile food additives which are contemplated for use in the methods and compositions of the present invention, there can be mentioned, by way of example, flavoring agents, preservatives, antioxidants, sweetening agents, vitamins and coloring agents. Illustrative of such additives are flavors such as vanillin, aromatic flavoring oils such as lemon oil, cinnamon oil, oil of anise, oil of bitter almond or benzaldehyde, oil of clove, oil of orange, oil of peppermint, garlic oil, onion oil and menthol; sweeteners such as aspartame and saccharin; colors such as methyl yellow as well as natural colors; preservatives such as methylparaben, propylparaben, chlorbutol, benzoic acid and salicylic acid; and antioxidants such as butylated hydroxyanisol. Some food additives may also be classified as drugs, e.g., the vitamins, discussed in more detail hereinbelow.

In the case of cosmetic additives contemplated for use in the methods and compositions of this invention, many of the same classes of ingredients (including some of the same specific ingredients) noted above as food additives are intended; in some cases, cosmetic additives may also be classified as drugs as discussed more fully below, for example, the vitamins, including the retinoids. Illustrative classes of cosmetic additives include preservatives, antioxidants, aromatic oils (fragrances), coloring agents and vitamins (also noted as drugs herein). Specific additives of interest for cosmetics include fragrant aromatic oils such as lavender oil, pine oil, oil of geranium, oil of rose, oil of sweet bay, oil of lemon, oil of lemon grass, preservatives such as camphor and vitamins such as vitamin $D_2$ (cholecalciferol), vitamin $D_3$, and vitamin E, as well as vitamin A and the other retinoids such as retinoic acid.

With regard to agrochemicals, those contemplated for use in the methods and compositions of this invention include pesticides (including, for example, insecticides and nematocides), fungicities, herbicides and plant growth regulators. Illustrative of such agrochemicals are pesticides such as pentachlorophenol, mevinphos, piperonyl butoxide, hydroprene, methoprene and kinoprene; fungicides such as 4-chloro-3-methylbenzothiazolone and pyrrolnitrin; and herbicides such as pentachlorophenol and 2,6-dichlorobenzonitrile. Yet other agrochemicals contemplated for use in the instant methods and compositions include herbicides such as atrazine, barban, bromoxynil, butachlor, carbetamide, chlorpropham, chlortoluron, 2,4-D, 2,4-DB, diallate, diearuba, dichlorprop, diuron, EPTC, ethofumesate, fluometuron, ioxynil, isoproturon, linuron, MCPA, mecoprop, metamitron, methabenzthiazuron, metribuzin, oxadiazon, pebulate, phenmedipham, prometryn, propachlor, propanil, propham, simazine, thiobencarb, triallate and trifluralin; fungicities such as 2,6-dimethyl-4-tridecylmorpholine, methyl N-(1-butylcarbarmoylbenzimidazol- 2-yl)carbamate, 1,2-bis(3-methoxycarbonyl-2-thioureido)benzene, isopropyl 1-carbamoyl-3-(3,5-dichlorophenyl)hydantoin and 1-(4-chlorophenoxy)-3,3-dimethyl- 1-( 1,2,4-triazol-1-yl)butan-2-one; ataricities such as dicofol and antiparasitic antibiotics, such as ivermectin, avermectins and milbemycins, which are also insecticidal; and insecticides such as chlorpyrifos, dementon-S-methyl, disulfoton, ethoprofos (or ethoprop), fenitrothion, malathion, parathion, phosalone, cyfuthrin, cypermethrin, deltamethrin, fenpropathrin, fenvalerate, permethrin, bendiocarb, endosulfan, lindane, and synthetic pyrethroids, for example, permetrin and cypermethrin.

It is well-known that a number of food and cosmetic additives, particularly flavors, fragrances and colors, as well as agrochemicals (pesticides, herbicides, insecticides and fungicides) can be complexed with cyclodextrin. Such materials exhibit significantly increased complexation and water solubility, however, when used in the methods and compositions of the present invention.

Among the lipophilic and/or water-labile drugs which are contemplated for use in the methods and compositions of the present invention, there can be mentioned antineoplastics (anticancer/antitumor agents), sedatives, antiinflammatory steroids (glucocorticoids), tranquilizers, anticonvulsants, antivirals, antihistaminics, vitamins/nutritional factors, emetics, anticoagulants, cardiotonics (including cardiac glycosicles), diuretics, non-steroidal analgesic and/or anti-inflammatory agents (NSAID's), androgens, estrogens, anabolic agents, vasodilators, anticlepressants, antipsychotics, hypnotics, antifungals, progestins, antiprotozoals, anthelmintics, anesthetics, vasoconstrictors, hypoglycemics, antibacterials/antibiotics, and anti-infectives, platelet inhibitors, muscle relaxants, antiemetics, radiodiagnostics, antispasmodics, antiarrythmics, carbonic anhydrase inhibitors, gastrointestinal agents (including $H_2$-antagonists and other anti-ulcer agents), antihypertensives especially including those useful as anti-glaucoma agents, serotonin antagonists, narcotic antagonists, narcotic agonists, mixed narcotic agonists-antagonists, pharmacologically active proteins such as peptide hormones, enzymes, antibodies and other biologically produced substances, anti-Parkinsonism/dopamineric agents and drugs for treating Alzheimer's disease.

It is now well-known that lipophilic and/or water-labile drugs which complex with cyclodextrin have the required shape and size to fit at least partially into the cavity of the hydrated cyclodextrin molecule; see, for example, Brauns and Mtiller European Patent No. 0149197 B1. Drugs whose water solubility can be improved by complexation with cyclodextrins exhibit significantly increased complexation and water solubility when treated in accord with the present invention.

Specific drugs contemplated for use in the methods and compositions of the present invention include antineoplastics such as chlorambucil, lomustine, melphalan, methotrexate, hexamethylmelamine, teniposide, etoposide, semustine (methyl CCNU), fazarabine (Ara-AC), mercaptopurine, tubulazole, carmofur, carmustine, amsacrine, doxorubicin, bruceantin, diaziquone, dideminin B, echinomycin and PCNU; anti-inflammatory steroids such as betamethasone, fludrocortisone, dexamethasone, cortisone, hydrocortisone, triamcinolone, triamcinolone acetonide, prednisone and prednisolone; estrogens such as 17β-estradiol, 17α-ethynylestradiol (ethinylestradiol), ethynylestradiol 3-methyl ether, estrone, mestranol and estriol; progestins such as dimethisterone, norethindrone, norethindrone acetate, norgestrel, norethynodrel, ethisterone, medroxyprogesterone acetate and progesterone; anticonvulsants such as phenytoin (diphenylhydantoin) and carbamazepine; barbiturates such as pentobarbital, phenobarbital and secobarbital, variously useful as hypnotics, anticonvulsants and sedatives; antivirals such as acyclovir, trifluridine, zidovudine, vidarabine and virazole (also known as ribavirin); vitamins/nutritional factors such as retinol (vitamin A), vitamin A-acetate, cholecalciferol, retinal, retinoic acid (also know as tretinoin or Retin-A™), isotretinoin, etretinate, acitretin and B-carotene, collectively referred to herein as retinoids, as well as other fat-soluble vitamins such as the E, D and K vitamins; β-blockers such as timolol and atenolol, propranolol and nadolol, of interest not only as antihypertensives but also as anti-glaucoma agents; emetics such as apomorphine; diuretics such as chlorthalidone, furosemide and other sulfonamide-type diuretics and spironolactone, an aldosterone antagonist-type diuretic; anticoagulants such as dicumarol; cardiotonics such as digoxin and digitoxin; non-steroidal analgesics and/or anti-inflammatory agents such as aspirin, ibuprofen, indomethacin, piroxicam, sulindac and flurbiprofen; androgens such as 17-methyltestosterone and testosterone; mineral corticoids such as desoxycorticosterone; steroidal hypnotics/anesthetics such as alfaxalone; anabolic agents such as fluoxymesterone and methanstenolone; antidepressams such as sulpiride; antibiotics such as ampicillin and penicillin G; anti-infectives, such as benzalkonium chloride, cetylpyridinium chloride and chlorhexidine; coronary vasodilators such as nitroglycerin, flunarizine, lidoflazine and mioflazine; hypnotics such as etomidate; carbonic anhydrase inhibitors such as acetazolamide, chlorzolamide, ethoxzolamine, methazolamide, L-671,152 and MK-927; antifungals such as imidazole-type antifungals, e.g., econazole, clotrimazole, oxiconazole, bifonazole, metronidazole (metronidazole benzoate), fenticonazole, miconazole, sulconazole, tioconazole, isoconazole, butoconazole, ketoconazole, doconazole, parconazole, orconazole, valconazole and Iombazole, and trizole-type antifungals, e.g., terconazole and itraconazole; antiprotozoals such as imidazole-type antiprotozoals, e.g. , metronidazole, ornidazole, camidazole, ipronidazole, tinidazole and nimorazole, and benzimidazole-type antifungals, e.g., flubendazole; $H_2$-antagonists, including those of the imidazole-type, e.g., burimamide, metiamide, cimetidine and oxmetidine; imidazole-type antineoplastics, such as tubulazole, a microtubule inhibitor; anthelmintic agents, including those of the benzimidazole-type, for example, thiabendazole, oxibendazole, cambendazole, fenbendazole, flubendazole, albendazole and oxfendazole; antihistaminics, including benzimidazoles such as astemizole, piperidines such as levocabastine and piperazines such as flunarizine, oxatomide and cinnarizine; antipsychotics, including those of the piperidine-type such as fluspirilene, pimozide and penfluridole; gastrointestinal agents, including piperidine derivatives such as loperamide and cisapride; serotonin antagonists, for example those of the piperidine-type such as ketanserin, ritanserin and altanserin, and those of the piperazine-type such as mianserin (also an antihistaminic); anesthetics such as lidocaine; hypoglycemics such as acetohexamide; antiemetics such as dimenhydrinate; antibacterials such as cotrimoxazole; dopaminergic agents such as L-DOPA; anti-Alzheimer's agents such as THA; famotidine, an anti-ulcer agent/$H_2$-antagonist; benzodiazepines, for example chlordiazepoxide, diazepam, medazepam, oxazepam, lorazepam, flunitrazepam, estazolam, flurazepam, loprazolam, lormetazepam, nitrazepam, quazepam, temazepam and triazolam, variously useful as sedatives, hypnotics, anticonvulsants, tranquilizers and muscle relaxams; prostaglandins, for example PGE's such as $PGE_1$ (alprostadil), a vasodilator, and $PGI_2$ (prostacyclin or epoprostenol), a platelet inhibitor; angiotensive converting enzyme inhibitors (ACE inhibitors), such as enalaprilic acid (the diacid, sometimes called 'enalaprilate'), the ethyl ester of enalaprilic acid (sometimes called enalapril), captopril, lisinopril and SCH-33861, useful as antihypertensives; tetracycline antibiotics, such as tetracycline, chlortetracycline, oxytetracycline, demeclocycline, methacycline, doxycycline and minocycline; and macrolide antibiotics, such as erythromycin, josamycin, rosamycin, tylosin, troleandomycin and spiramycin.

In one particularly preferred aspect of the present invention, the drug contemplated for use herein is a carbonic anhydrase inhibitor, especially acetazolamide.

In another preferred aspect of the invention, the drug contemplated for use herein is a steroid, particularly an anti-inflammatory steroid (glucocorticoid), or a steroidal estrogen, progestin, anabolic agent, androgen, anesthetic/hypnotic or diuretic/aldosterone antagonist.

In another preferred aspect of the invention, the drug contemplated for use herein is a benzodiazepine sedative or an antibiotic, antiviral, antifungal or anti-infective agent.

In another preferred aspect of the invention, the drug contemplated for use herein is an ACE inhibitor, especially enaprilic acid or enalapril.

In still another preferred aspect of the invention, the drug contemplated for use herein is a β-blocker.

In yet another preferred aspect of the invention, the drug contemplated for use herein is the reduced, dihydropyridine form of a dihydropyridine ⇌ pyridinium salt redox system for brain-targeted drug delivery.

With respect to the redox system for brain-targeted drug delivery, the following definitions are applicable:

The term "lipoidal" is intended to designate a redox moiety which is lipid-soluble or lipophilic.

The terms "redox carrier system" and "redox analog system" are intended to designate two different approaches to targeting drugs to the brain using a dihydropyridine ⇌ pyridinium salt system; compounds representing either of these approaches are contemplated for use in the present invention.

The redox carrier system provides for brain-targeted drug delivery by means of carrier-drugs, which in their reduced form, which is the form intended for administration, can be represented by the formula

[D-DHC]

wherein [D] is a centrally acting drug species and [DHC] is the reduced, biooxidizable, blood-brain barrier penetrating, lipoidal form of a dihydropyridine ⇌ pyridinium salt redox carrier. In their oxidized form, which is the form "locked" in the brain from which the active drug is ultimately released, the carrier-drugs can be represented by the formula

[D-QC]$^+$ X$^-$ wherein X$^-$ is the anion of a non-toxic pharmaceutically acceptable acid, [D] is a centrally acting drug species and [QC]$^+$ is the hydrophilic, ionic pyridinium salt form of a dihydropyridine ⇌ pyridinium salt redox carrier. The various redox approaches are now well-known, having been described in many patents and literature articles; the originator of the redox technology, Nicholas S. Bodor, has also described the use of cyclodextrin derivatives in conjunction with the reduced, dihydropyridine forms of the redox systems, e.g., in Bodor U.S. Pat. Nos. 4,983,586; 5,002,935; 5,017,566; and 5,024,998. While the redox systems for use herein can be any of those defined in the Bodor patents, those in which the centrally acting drug species and redox carriers are indicated in the Bodor patents as being preferred are likewise preferred for use herein. Thus, preferred redox carrier compounds of the formula [D-DHC] are those in which [D], the centrally acting drug species, is a dopaminergic agent, an androgenic agent, an anticonvulsant, an anxiolytic agent, a neurotransmitter, an antibiotic or antibacterial agent, an antidepressant, an antiviral agent, an anticancer or antitumor agent, an antiinflammatory agent, an estrogen or a progestin, particularly when the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU. Especially preferred redox carrier compounds of the formula [D-DHC] are:

1-methyl-3-{{N-{β-[3,4-bis(pivalyloxy)phenyl] ethyl}carbamoyl}}-1,4-dihydropyridine, 1-methyl-3-{N-[[β-[3,4-bis(isobutyryloxy)phenyl]-ethyl] ]}carbamoyl-1,4-dihydropyridine and N-{β-[3,4-bis(pivalyloxy)phenyl] ethyl} aminocarbonyloxymethyl 1,4-dihydro- 1-methyl-3-pyridinecarboxylate, which are dopamine derivatives;

17β-[(1,4-dihydro-1-methyl-3-pyridinylcarbonyl)oxy]androst-4-en-3-one and 17β-{ [(3"-carbamoyl-1',4'-dihydropyridinyl)acetyl]oxy} androst-4-en-3-one, which are testosterone derivatives;

5,5-diphenyl-3-[(1-methyl-1',4'-dihydropyridin-3'-yl)carbonyloxymethyl] -2,4-imidazolidinedione, 3-[ (3"-carbamoyl-1',4'-dihydropyridin- 1'-yl)acetyloxymethyl] -5,5-diphenyl-2,4-imidazolidinedione and 3-[3'-(3"-carbamoyl- 1",4"-dihydropyridin-1"-yl)propionyloxymethyl]-5,5-diphenyl-2,4-imidazolidinedione, which are phenytoin derivatives;

1-methyl-3-N-[ 3-(benzyloxycarbonyl)propyl]carbamoyl- 1,4-dihydropyridine and 1-methyl-3-{N-[(3'-cyclohexylcarbonyl)propyl]}-carbamoyl- 1,4-dihydropyridine, which are GABA derivatives;

1-methyl-3-[2'-(2"-propyl)pentanoyloxy]ethylcarbamoyl-1,4-dihydropyridine, 1-methyl-3-[2'-(2"-propyl)pentanoyloxy]ethoxycarbonyl- 1,4-dihydropyridine and 1-[2'-(2"-propyl)pentanoyloxy]ethyl-3-carboxamide- 1,4-dihydropyridine, which are valproic acid derivatives;

1-methyl-3-{N-[(1'-ethoxycarbonyl)-2'-(4"-pivaloyloxyphenyl)ethyl]}-carbamoyl- 1,4-dihydropyridine and 1-methyl-3-{N-[(1'-ethoxycarbonyl)-2'-( 4"-isobutyryloxyphenyl)ethyl]}carbamoyl-1,4-dihydropyridine, which are tyrosine derivatives;

[[(1,4-dihydro-1-methyl-3-pyridinyl)carbonyl]oxy]methyl [2S-( 2α,5α,6β)]-3,3-dimethyl-7-oxo-6-[ (2,6-dimethoxy)benzamido]-4-thia-1-azabicyclo[ 3.2.0]heptane-2-carboxylate, [[(1,4-dihydro-1-methyl-3pyridinyl)carbonyl] oxy]methyl [2S-(2α,5α,6β)]-3,3-dimethyl-6-(5-methyl-3-phenyl- 4-isoxazolecarboxamido-7-oxo-4-thia- 1-azabicyclo[3.2.0]heptane-2-carboxylate, [[(1,4-dihydro-1-methyl-3-pyridinyl)carbonyl]oxy]methyl [2S-( 2α,5α,6β)]-3,3-dimethyl-7-oxo-6-[ (phenylacetyl)amino]-4-thia- 1-azabicyclo-[ 3.2.0]heptane-2-carboxylate, [[(1,4-dihydro-1-methyl-3-pyridinyl)carbonyl]oxy] methyl [2S-(2α,5α,662 )]-6-[3-(2-chlorophenyl)-5-methyl-4-isoxazolecarboxamido] -3,3-dimethyl-7-oxo-4-thia-1-azabicyclo[3.2.0]heptane-2-carboxylate and [[(1,4-dihydro-1-methyl-3-pyridinyl)carbonyl]oxy]methyl [2S-(2α,5α,6β)] -6-[3 -(2,6-dichlorophenyl)-5-methyl-4-isoxazolecarboxamido]-3,3-dimethyl-7-oxo-4-thia-1-azabicyclo[3.2.0]heptane-2-carboxylate, which are derivatives of methicillin, oxacillin, benzylpenicillin, cloxacillin and dicloxacillin, respectively;

[{ N-[ 3-(10,11-dihydro-5H-dibenz(b,f]azepin-5-yl)]propyl-N-methylamino} carbonyloxy]methyl 1,4-dihydro-1-methyl-3-pyridinecarboxylate and [ 1-{N-[3-(10,11-dihydro-5H-dibenz[b,f]azepin-5-yl)]propyl-N-methylamino} carbonyloxy]ethyl 1,4-dihydro-1-methyl-3-pyridinecarboxylate, which are derivatives of desipramine;

1-methyl-3-{[2-(9-guanylmethoxy)ethoxy]carbonyl}-1,4-dihydropyridine, which is a derivative of acyclovir;

3'-(1,4-dihydro-1-methyl-3-pyridinylcarbonyl)-5'-pivaloyltrifluorothyroidinc, which is a derivative of trifluorothymidine;

3'-azido-3'-deoxy-5'-(1-methyl-1,4-dihydro-3-pyridinyl) carbonyl] thymidine, which is a derivative of zidovudine (AZT);

N-(2-chloroethyl)-N'-[4-(1,4-dihydro-1-methyl-3-pyridinecarbonyloxy)cyclohexyl] -N-nitrosourea, N-(2-fluoroethyl)-N'-[2-(1,4-dihydro-1-methyl-3-pyridinecarbonyloxy)ethyl] -N-nitrosourea and N-(2-chloroethyl)-N'-[2-(1,4-dihydro- 1-methyl-3-pyridinecarbonyloxy)ethyl]-N-nitrosourea, which are derivatives of hydroxy-CCNU, FENU and HENU, respectively;

1-methyl-3-[ (N-{ 2-[4-({4-[bis(2-chloroethyl)]amino} phenyl)butanoyloxy] ethyl} )carbamoyl]-1,4-dihydropyridine, 1-methyl-3-(N-{ 4-[4-(4-{ [bis(2-chloroethyl)] amino}phenyl)butanoyloxy]cyclohexyl}carbamoyl)-1,4-dihydropyridine, 1-methyl-3-[(N-{ 2-[4-({4-bis(2-chloroethyl)]amino}phenyl)butanoyloxy] propyl}) carbamoyl]-1,4-dihydropyridine, 1-methyl-3-[ (N-{ 2-phenyl-2-({4-[bis(2-chloroethyl)]amino} phenyl) butanoyloxy)]} ethyl)carbamoyl] -1,4-dihydropyridine and 1-methyl-3-[N-({ 1-[4(4-{[bis(2-chloroethyl)] amino} phenyl)butanoyloxy]cyclohexyl} methyl)carbamoyl]-1,4dihydropyridine, which are derivatives of chlorambucil;

1-methyl-3-N-[2-(3-indolyl)ethyl]carbamoyl-1,4-dihydropyridine, which is a derivative of tryptamine;

9-fluoro-11β,17-dihydroxy-16α-methyl-21-{ [(1-methyl-1,4-dihydropyridin- 3-yl)carbonyl]oxy} pregna-1,4-diene-3,20-dione and 11/3, 17-dihydroxy- 21-{[(1-methyl-1, 4-dihydropyridin-3-yl)carbonyl]oxy} pregn-4-ene- 3,20- dione, which are derivatives of dexamethasone and hydrocortisone, respectively;

3-hydroxy-17/3-[(1-methyl-1,4-dihydropyridin-3-yl)carbonyl]oxyestra- 1,3,5(10)-triene, which is an estradiol derivative;

3-hydroxy-17β-{[ 1-methyl-1,4-dihydropyridin-3-yl)carbonyl]oxy}-19-nor- 17α-pregna-1,3,5(10)-trien-20-yne, 3-[(1-methyl-1,4-dihydro-3-pyridinyl)carbonyloxy]estra-1, 3,5(10)-trien-17-one, 17β-[(1-methyl-1,4-dihydro- 3-pyridinyl)carbonyloxy]estra-1,3,5(10)-trien-3-ol 3-methyl ether, 3,17β-bis-{[(1-methyl-1,4-dihydropyridin-3-yl)carbonyl] oxy}estra-1,3,5(10)-triene, 3-(phenylcarbonyloxy)-17β-{ [(1-methyl-1,4-dihydropyridin-3-yl)carbonyl] oxy}estra-1, 3,5(10)-triene and 3-methoxy-17β-{[ 1-methyl-1,4-dihydropyridin- 3-yl)carbonyl]oxy}-19-nor-17β-pregna-1,3,5(10)- trien-20-yne, which are derivatives of ethinyl estradiol, estrone, estradiol 3-methyl ether, estradiol benzoate and mestranol, respectively;

17β-{ [(1-methyl-1,4-dihydropyridin-3-yl)carbonyl] oxy}-19-norpregn-4-en- 20-yn-3-one, 17β-{ [(1-methyl-1, 4-dihydropyridin-3-yl)carbonyl]oxy}-pregn- 4-en-20-yn-3-one, 13-ethyl-17β-{[(1-methyl-1,4-dihydropyridin-3yl)carbonyl] oxy}-18,19-dinorpregn-4-en-20-yn-3-one and 17β-{[(1-methyl- 1,4-dihydropyridin-3-yl)carbonyl]oxy}-19-norpregn-5(10)-en-20-yn-3-one, which are derivatives of norethindrone, ethisterone, norgestrel and norethynodrel, respectively;

1-methyl-3-[N-(2-{ 1-(p-chlorobenzoyl)-5-methoxy-2-methyl-3-indolyl] acetoxy}ethyl)carbamoyl]-1,4-dihydropyridine and 1-methyl-3-{N-[2-(6-methoxy-α -methyl-2-naphthalenylacetoxy)ethyl]carbamoyl-1,4-dihydropyridine, which are derivatives of indomethacin and naproxen, respectively; and 3-(1,4-dihydro-1-methyl-3-pyridinylcarbonyloxymethyl)-5-fluorouracil and 1-(1,4-dihydro-1-methyl-3-pyridinecarbonyloxymethyl)-5-fluorouracil, which are derivatives of 5-FU (5-fluorouracil).

In the discussion that follows, the particulars of the present invention are discussed with respect to drugs. It is to be understood, however, that except where the discussion focuses on matters which are obviously unique to drugs (such as bioavailability), the particulars are the same when a food additive, cosmetic additive or agrochemical is used instead of a drug herein.

Quite surprisingly, it has now been found that is possible to increase the effects of cyclodextrin complexation by adding small amounts of water-soluble, pharmaceutically acceptable, pharmacologically inactive polymers to aqueous cyclodextrin/drug solutions and then heating the solutions for some time. Typically, the polymer is dissolved in an aqueous solution of the cyclodextrin, or both polymer and cyclodextrin are dissolved in water, and then the drug is added. The cyclodextrin concentration can range from about 0.1 to 70% w/v and the polymer concentration from about 0.001 to about 5% w/v, preferably from about 0.01 to about 0.5% w/v, in the original solution. The polymer: cyclodextrin weight ratio can range from about 1:4 to about 1:50,000, but is usually from about 1:4 to about 1:10,000, that is, 1 part of polymer to 4 to 10,000 parts of cyclodextrin, and is preferably from about 1:100 to about 1:10,000, more preferably from about 1:100 to about 1:1,000, i.e., 1 part of polymer to from 100 to 1,000 pans of cyclodextrin. Another useful range for the weight ratio of polymer to cyclodextrin is from about 1:1 to about 1:5,000, especially from about 1:4 to about 1:5,000, or from about 1:500 to about 1:5,000. Since maximum complexation is ordinarily desired, the drug is usually added in excess. On a molecular basis, the ratio of drug to cyclodextrin will be in the range previously known/ determined for drug/cyclodextrin complexes lacking the polymer used herein, typically from about 0.33 to about 3.0 molecules of drug per molecule of cyclodextrin in the co-complex.

In the preceding paragraph, it is indicated that the drug is added in excess to achieve maximum complexation. This refers only to the preparation of the complex, not to preparation of the ultimate pharmaceutical or other composition intended for its final use. In the latter situation, a slight excess of the cyclodextrin (for example, approximately 10% excess) is used over the amount calculated to dissolve the active ingredient so as to avoid precipitation of the drug or other active ingredient during storage (as may result, for example, from fluctuations in temperature). Also in the preceding paragraph, reference to a molecular ratio of 0.33 to 3.0 refers to the ratio of drug to cyclodextrin in the complex, not to the number of molecules in a solution. Because the complexation is an equilibrium process, a large number of cyclodextrin molecules are usually used in the process of complexing a few molecules of a drug molecule. Most of the cyclodextrin molecules in the aqueous complexation medium do not form a complex with the drug molecules.

The drug may be dissolved in the cyclodextrindpolymer solution before, during and/or after the cyclodextrin/polymer solution has been kept at from about 30° to about 150° C. for a period of from about 0.1 to about 100 hours. It is believed that the polymer and cyclodextrin molecules must be activated to obtain the desired degree of complexation enhancement. The simplest way to activate the molecules is to heat the aqueous solution containing polymer and cyclodextrin. Heating can be accomplished in many different ways. In a preferred embodiment, the polymer-cyclodextrin solution is heated in a sealed container in an autoclave (120° C. for approximately 20 minutes). Good results have also been accomplished by sonicating the polymer-cyclodextrin solutions (which typically raises the temperature to above 30° C., e.g., to 40° C. or higher). Very good results have also been obtained by heating the polymer-cyclodextrin solutions in a microwave oven (e.g., 40° C. for about 5 minutes). Typically, the drug is present during heating of the polymer-cyclodextrin solution.

Optionally, the polymer and cyclodextrin can be combined in aqueous solution, with heating at the temperature and for the time indicated in the preceding paragraph and dried (preferably lyophilized) to give a cyclodextrin/polymer combination complexing agent. That complexing agent can subsequently be combined in aqueous solution with the drug, with or without heating for the time and at the temperature indicated above. Whatever the manner of preparing the drug/cyclodextrin/polymer aqueous solution, said solution can optionally be dried in accord with methods which are known per se. Depending on the drug employed, acid or base may be added to the cyclodextrin/polymer/drug solution during preparation.

As will be apparent from the Examples hereinafter, one can readily determine the concentration at which a given water-soluble polymer exerts a maximum solubilizing/stabilizing/complexing effect on a given drug and a given cyclodextrin in aqueous medium. It is generally disadvantageous to use a significant amount of polymer in excess of that needed to achieve the maximum effect. Excess polymer can actually decrease the desired solubilizing/stabilizing/complexing effect, and can tend to increase the viscosity of the aqueous medium in which complexation occurs. The amount of polymer used should be sufficient to enhance stabilization/solubilization/complexation, but insufficient to cause a significant increase in viscosity upon heating. Increase in viscosity to a gel-like or near gel-like stage should be avoided when carrying out the stabilization/solubilization/complexation processes of the invention. Obviously, once the process has been completed, the resultant mixture can be made more viscous if desired in the pharmaceutical or other compositions provided by the present invention.

Aqueous solutions of cyclodextrins and polymers prepared in accord with the present invention have a greater solubilizing and stabilizing effect on lipophilic and/or water-labile drugs than cyclodextrin solutions made by simply dissolving cyclodextrins in water or aqueous buffer solutions. The water-soluble pharmaceutical polymers increase the solubilizing effect of the cyclodextrins and, thus, make it possible to reduce the amount of cyclodextrin which will be present in the pharmaceutical composition ultimately administered. Aqueous cyclodextrin/drug formulations containing water-soluble pharmaceutical polymers are characterized by fast and efficient drug release, which can result in a more rapid onset of the desired therapeutic response and better total bioavailability of the drugs. Solid pharmaceutical preparations, made, for example, by removal of water from the above-mentioned aqueous cyclodextrin-polymer-drug solutions, for example by lyophilization, are characterized by faster and more efficient dissolution of drugs compared to the dissolution of drugs from solid cyclodextrin preparations without polymers. This can lead to hastening the onset of the therapeutic response and can also increase the total bioavailability of drugs from solid pharmaceutical preparations. Moreover, the drug/cyclodextrin/polymer co-complex is adsorbed onto biological membranes, such as the skin and the cornea of the eye, and this results in greater drug bioavailability compared to simple drug/cyclodextrin complexes.

It appears that the water-soluble polymers used in accord with the present invention alter the hydration of the cyclodextrin molecules and thus their three-dimensional structure in aqueous solutions. Heating accelerates this process. It also appears that the polymer participates directly in the drug complex formation, acting as a co-complexing agent with the cyclodextrin. S. H. S. Leung, J. R. Robinson and V. H. L. Lee ["Parenteral Products", Chapter 10 in *Controlled Drug Delivery. Fundamentals and Applications*, second edition, J. R. Robinson and V. H. L. Lee, editors, Marcel Dekker, Inc., New York, 1987, pp.433–480], in a review of studies from the 1950's and early 1960's, point out that the role of plasma protein and tissue binding in prolonging drug action is well-known, and that the same result can be achieved by forming a dissociable complex of a drug with macromolecules such as methylcellulose, carboxymethylcellulose and polyvinylpyrrolidone. Table 1 and Table 6 hereinbelow show that aqueous polymer solutions ($S_2$) solubilize drugs to a greater extent than pure water ($S_1$). This can be attributed to complexation of the drug with the polymer. Thus, the polymers and the cyclodextrins both form soluble complexes with various drug molecules and can be used to increase the aqueous solubility of the drugs. However, when polymer and cyclodextrin are mixed together in accord with the present invention, one obtains greater drug solubility enhancement than when the polymer and cyclodextrin are used separately; indeed, the combination effect is more than simply additive, it is synergistic. This is indicative of the formation of a new type of complex between the drug and the polymer-cyclodextrin. The cyclodextrin can thus be considered to be the complexing agent, the polymer a co-complexing agent, and the drug complex not simply a drug/cyclodextrin complex, but a drug/cyclodextrin/polymer co-complex.

While not wishing to be bound by any particular theory, it is believed that the mechanism of polymer/cyclodextrin/drug complexation is similar to the mechanism involved in the complexation of polymers and micelies. Interactions between surfactants and polymers were observed in the late fifties and early sixties (Artwood et al.: *Surfactant Systems. Their Chemistry, Pharmacy and Biology*, Chapman and Hall, London, 1983, pp. 361–365). The surfactant-polymer interactions are either between individual surfactant molecules and the polymer chain (i.e., simple adsorption), or in the form of polymer-aggregate complexes (i.e., complex formation between the micelles and the polymer chain). The formation of such structures in surfactant-polymer systems is often illustrated as resembling a string of pearls or water droplets on a spider's web (Myers, *Surfactant Science and Technology*, VCH Publishers, New York, 1988, pp. 142–145). Addition of water-soluble polymers to aqueous surfactant solutions has been found to increase the solubilizing effects of the suffactants. Polymer-suffactant complexes, e.g., the PVP-sodium laurylsulfate complex, have a larger solubilizing effect than the sum of the individual solubilizing effects of the polymer and the surfactant. That is, the polymer has a synergistic effect on the capacity of the surfactant to solubilize water-insoluble compounds such as an oil-soluble dye. For example, addition of 0.1% PVP about doubles the solubilizing effect of the non-ionic surfactant dodecyl-(oxyethylene)-ether (Attwood et al, *Surfactant Systems. Their Chemistry, Pharmacy and Biology*, Chapman and Hall, London, 1983, pp. 361–365). It is believed that the water-soluble polymer interacts with the cyclodextrin and drug in the course of complex formation to form a stabilized complex of drug and cyclodextrin co-complexed or double complexed with the polymer to form a "string of pearls" or double complex of the type (drug-cyclodextrin)-polymer. This complex is always more stable than the drug-cyclodextrin complex or the drug-polymer complex. This is the basis for the synergistic effect of the polymers on cyclodextrin solubilization of water-insoluble drugs.

The effect of this proposed mechanism on the delivery of drugs through biological membranes can be explained as follows: The forces keeping the drug-cyclodextrin complex and the polymer together are rather weak and are readily broken, releasing the drug-cyclodextrin complex, which then becomes weaker and more prone to dissociation (i.e., to release of the free drug molecules). The present invention uses this property of the (drug-cyclodextrin)-polymer complex to increase the bioavailability of drugs from aqueous drug-cyclodextrin solutions into the skin and eye. The bioavailability enhancing effects of the polymers can be explained in the following way:

When water-soluble polymers are added to the cyclodextrin media, the polymers increase the complexation of drugs; therefore, when polymers are used, less cyclodextrin is needed than when cyclodextrin is used alone to solubilize the drug in an aqueous drug formulation. When the drug-cyclodextrin-polymer solution comes into close contact with a biological membrane (e.g., the skin or the cornea of the eye), then the polymer is adsorbed onto the membrane, releasing the drug-cyclodextrin complex; then, the drug-cyclodextrin complex becomes unstable, releasing the drug into the solution. When released, the free drug first partitions into and then penetrates through the membrane. The absorption of the polymer only occurs in the micro-environment close to the membrane. This ensures that the drug molecules are only released from the cyclodextrin complex close to the membrane and not out in the bulk solution. Thus, supersaturated drug solution is formed in the micro-environment at the membrane surface. In this supersaturated micro-environment, the drug molecules have a very high activity and, thus, the system is unstable and seeks to stabilize itself by releasing energy. To do this, the lipophilic drug molecules can either form a molecular aggregate [i.e., solids such as crystals (precipitation)] or partition into the lipophilic biological membrane. Supersaturation itself is insufficient to cause crystals to form; the crystal embryos must form by collision of drug molecules in the solution (Florence et al, *Physiochemical Principles of Pharmacy*, 2nd Ed., Macmillan Press, London 1988, p.24). Therefore, the system lowers its energy by releasing the drug molecules into the membrane. The high thermodynamic activity of the drug molecules at the membrane surface increases the flux of the drug through the membrane [Higuchi, "Physical chemical analysis of percutaneous absorption process from creams and ointments," *J. Soc. Costa. Chem.*, 11, 85–97 (1960); Loftsson, "Experimental and theoretical model for studying simultaneous transport and metabolism of drugs in excised skin", *Arch. Pharm. Chem., Sci. Ed.*, 10, 17–24 (1981)]. In this way, the polymers accelerate the permeability of the drug molecules through the membrane. In the aqueous drug/cyclodextrin solutions (vehicles), the polymers act as permeability enhancers.

It is well-known that macromolecules, such as proteins and various polymers, adsorb at interfaces such as skin, mucosa and the cornea of the eye. This property of macromolecules is sometimes called muco-adhesion. [Chien, *Novel Drug Delivery Systems*, 2nd Ed., Marcel Dekker, New York 1992, page 173; Florence et al, *Physicochemical Principles of Pharmacy*, 2nd Ed., Macmillan Press, London 1988, pp. 297–298; N. A. Peppas et al, "Surface, interfacial and molecular aspects of polymer bioadhesion on soft tissues", in J. M. Anderson and S. W. Kim (editors), *Advances in Drug Delivery Systems*, Elsevier, Amsterdam 1986, pp. 257–275.) This is supported by Examples 15, 15a and 18 hereinbelow.

Pharmaceutical compositions utilizing the drug/cyclodextrin/polymer products prepared in accord with the present invention can be used to treat a variety of conditions, depending upon the pharmacological nature of the drug selected for administration. The compositions contain a pharmacologically/therapeutically effective amount of the selected drug and the amounts/ratios of selected cyclodextrin and selected polymer noted hereinabove, together with a non-toxic, pharmaceutically-acceptable carrier. For example, if the selected drug is an anti-inflammatory agent, a pharmacologically effective amount thereof will be an amount sufficient to elicit an anti-inflammatory response. Selection of the cyclodextrin and the polymer in the compositions will depend upon the nature of the drug and the contemplated route of administration. Virtually any route of administration by which a selected drug can be used can be employed for the instant compositions, including but not limited to parenteral, oral and topical (including ophthalmic) routes. Polymers and cyclodextrins as defined herein will be selected according to the contemplated route of administration, since some may be acceptable for certain routes of administration and not for others. For example, a hydroxy-alkylated cyclodextrin such as hydroxypropyl-β-cyclodextrin rather than an alkylated cyclodextrin would be selected for intravenous use because of toxicity considerations. Similarly, only some of the polymers disclosed herein may be suitable for intravenous use, as is indeed well-known in the art.

In the case of parenteral formulations, intended, for example, for intramuscular, subcutaneous, intra-articular or intravenous administration, the pharmaceutical composition of drug/cyclodextrin/polymer will be in the form of an aqueous solution which is acceptable for parenteral administration, i.e., which is sterile and pyrogen-free and has been prepared in accord with accepted pharmaceutical procedures, for example as described in *Remington's Pharmaceutical Sciences*, seventeenth edition, ed. Alfonso R. Gennaro, Mack Publishing Company, Easton, Pa. (1985), pp. 1518–1552. The aqueous sterile injection solutions may further contain anti-oxidants, buffers, bacteriostats, isotonicity adjusters and like additions acceptable for parenteral formulations. Various unit dose and multidose containers, e.g., sealed arepules and vials, may be used, as is well-known in the art. The essential ingredients of the sterile parenteral formulation, i.e., the drug(s), water and selected cyclodextrin(s) and polymer(s), may be presented in a variety of ways, just so long as the solution ultimately administered to the patient contains the appropriate amounts of the essential ingredients. Thus, for example, the drug/cyclodextrin/polymer/water formulation may be presented in a unit dose or multidose container, ready for injection. As another example, a concentrated solution of drug/cyclodextrin/polymer/water may be presented in a separate container from a diluting liquid (water or cyclodextrin/water) designed so that the contents can be combined to give a formulation containing appropriate amounts for injection. As another alternative, the drug or a drug/cyclodextrin/polymer combination may be provided in a freeze-dried condition in one container, while a separate container contains diluting liquid (water or cyclodextrin/water, depending on the amount of cyclodextrin in the other container), again designed so that the contents can be combined to give a formulation containing the appropriate amounts of the essential ingredients. As yet another alternative, the cyclodextrin/polymer may be provided in a freeze-dried condition in one container, the drug in another and the diluting liquid in yet another container. In any event, the contents of each container will be sterile.

For oral administration, the pharmaceutical compositions may be in the form of any well-known oral dosage form, e.g., tablets, caplets, capsules, pills, powders, solutions, gels and the like. Orally acceptable carrier materials, including excipients, binders and disintegrators, are well-known in the art. Moreover, the usual buffers, coloring agents, flavoring agents and sweetening agents can be added, if necessary or if desired. Tablets and caplets may also be coated with the usual coating materials.

In addition to oral dosage forms which are intended to be swallowed, the present invention contemplates oral dosage forms which are intended for usage only in the oral cavity, typically mouthwashes, and those which are intended for buccal and/or sublingual administration (such as lozenges).

For rectal or vaginal administration, suppositories may be suitable, appropriate carriers for which are well-known. Similarly, for topical use, well-known topically acceptable carriers/vehicles can be employed to form creams, gels, ointments and the like. Appropriate carriers for use in nasal dosage forms (solutions, gels, ointments and the like) are similarly well-known.

In the case of ophthalmic compositions, the carrier must be a non-toxic, ophthalmically acceptable carrier. Suitable ophthalmic carriers will be apparent to those skilled in the art of ophthalmic formulations. Obviously, the choice of suitable carriers will depend on the exact nature of the particular dosage form desired, e.g., whether the drug/cyclodextrin/ polymer complex is to be formulated imo an ophthalmic solution or suspension (typically for use as eye drops), an ophthalmic ointment or cream or an ophthalmic gel. Preferred dosage forms are solutions, which contain a major amount of water in addition to the active ingredient. Minor amounts of other ingredients such as pH adjusters (e.g., a base such as NaOH), emulsifiers or dispersing agents, buffering agents, preservatives, wetting agents and jelling agents may also be present. Most preferably, the ophthalmic composition is a sterile, isotonic, buffered aqueous solution.

Especially preferred pharmaceutical compositions provided by the present invention include ophthalmic formulations (e.g., eyedrops) containing a carbonic anhydrase inhibitor, such as acetazolamide, an ACE inhibitor such as enalaprilate or enalapril, a/3-blocker active as an anti-glaucoma agent such as timolol, an antiviral or an antibiotic, oral formulations such as mouthwashes or buccal tablets containing an anti-inflammatory steroid, e.g., hydrocortisone, dexamethasone or triamcinolone acetonide, and/or an antifungal, antiviral or anti-infective/antiseptic agent; oral formulations such as sublingual tablets containing a benzodiazepam such as flunitrazepam, for treatment of insomnia; and sublingual tablets comprising an estrogen, progestin or androgen (such as 17β-estradiol for treatment of postmenopausal symptoms in women) or an anti-infective agent (e.g., benzalkonium chloride).

Generally speaking, the therapeutic dosage ranges for administration of drugs in the pharmaceutical formulations described herein will be the same as or less than (in some instances, substantially less than) those characteristically used for administration of the drug per se (or, in the case of the carrier-drugs, of the parent drug species per se). Naturally, such therapeutic dosage ranges will vary with the size and species of the patient, the condition for which the formulation is administered, the route of administration employed and the like. The quantity of given dosage form needed to deliver the desired dose of active ingredients will of course depend upon the concentration of the drug in the pharmaceutical formulation.

In a similar manner to the pharmaceutical compositions described above, compositions comprising the non-drug/ cyclodextrin/polymer products prepared according to the present invention will be formulated in accord with their intended use. A non-toxic, pharmaceutically acceptable carrier as used in the instant pharmaceutical compositions will normally meet or exceed the requirements for use in cosmetics, agrochemicals and even in foods. Such a carrier is therefore eminently well-suited for cosmetic, food and agricultural applications as well. Yet other carriers can be used for these other applications, however, just so long as they are acceptable for use in foods or cosmetics or agrochemicals, as the case may be. Thus, for example, an agriculturally acceptable carrier will be used with an agrochemical/cyclodextrin/polymer product, which will itself be present in an effective amount, i.e., a herbicidally effective amount when the agrochemical is a herbicide, a pesticidally effective amount when the agrochemical is a pesticide, a fungicidally effective amount when the agrochemical is a fungicide, and so forth. Appropriate carrier materials for use with food additives or cosmetic additives or agrochemicals, in addition to non-toxic, pharmaceutically acceptable carriers, will be apparent to those skilled in the food, cosmetic and agrochemical ans.

In order to further illustrate the present invention and the advantages thereof, the following specific examples are given, it being understood that same are intended only as illustrative and in no way limitative of the invention.

EXAMPLE 1

Solubilities (S) of various drugs in four different solvents, i.e., (a) water ($S_1$), (b) aqueous 0.25% (w/v) sodium carboxymethylcellulose solution (CMC) ($S_2$), (c) aqueous solution of 10% (w/v) 2-hydroxypropyl-β -cyclodextrin (HPβCD) of molar substitution (MS) = 0.6 ($S_3$) and (d) aqueous solution containing both 0.25% (w/v) CMC and 10% (w/v) HPβCD MS= 0.6 ($S_4$) were determined by adding an excess amount of the drug to be tested to the solvents and heating the suspensions formed in sealed containers to 120° C. The suspensions were kept at this temperature for 20 minutes and then allowed to equilibrate for 3 days at room temperature (approximately 23° C.). After equilibration, aliquots were filtered through 0.45 μm membrane filters, diluted with a mixture of methanol and water (7:3 v/v) and analyzed by an high pressure liquid chromatographic (HPLC) method. The results set forth in Table 1 show that the solubilizing effect of HPβCD was increased by 4 to 57% ($S_4/S_3$=1.04 to 1.57) when 0.25% CMC was present in the solution.

TABLE 1

The effect of CMC on the solubilization of various drugs in aqueous HPβCD solutions.

| Drug | $S_1$ (mg/ml) | $S_2$ (mg/ml) | $S_3$ (mg/ml) | $S_4$ (mg/ml) | $S_4/S_3$ |
|---|---|---|---|---|---|
| Acetazolamide | 0.70 | 0.84 | 2.52 | 3.11 | 1.23 |
| Alprazolam | 0.07 | 0.18 | 1.28 | 1.55 | 1.21 |
| Carbamazepine | 0.11 | 0.20 | 7.00 | 9.20 | 1.31 |
| Clotrimazole | 0.00 | 0.00 | 1.20 | 1.40 | 1.17 |
| Dexamethasone | 0.26 | 0.33 | 8.43 | 8.75 | 1.04 |
| Diazepam | 0.69 | 0.81 | 9.14 | 9.70 | 1.06 |
| Econazole | 0.57 | 0.60 | 4.86 | 7.41 | 1.52 |
| 17β-Estradiol | 0.01 | 0.17 | 5.10 | 5.35 | 1.05 |
| Ethoxyzolamide | 0.04 | 0.07 | 1.19 | 1.66 | 1.39 |
| Hydrocortisone | 0.36 | 1.10 | 12.88 | 17.02 | 1.32 |
| Miconazole | 0.04 | 0.06 | 1.98 | 2.50 | 1.26 |
| Oxazepam | 0.03 | 0.04 | 0.90 | 1.42 | 1.57 |
| Prednisolone | 0.38 | 0.53 | 13.60 | 15.30 | 1.13 |
| Progesterone | 0.00 | 0.00 | 4.03 | 6.11 | 1.52 |
| Sulfa- | 0.36 | 0.69 | 10.01 | 12.60 | 1.26 |

TABLE 1-continued

The effect of CMC on the solubilization
of various drugs in aqueous HPβCD solutions.

| Drug | $S_1$ (mg/ml) | $S_2$ (mg/ml) | $S_3$ (mg/ml) | $S_4$ (mg/ml) | $S_4/S_3$ |
|---|---|---|---|---|---|
| methoxazole | | | | | |
| Termazepam | 0.60 | 0.65 | 3.01 | 3.48 | 1.16 |
| Triamcinolone acetonide | 0.03 | 0.07 | 2.09 | 2.58 | 1.23 |

EXAMPLE 2

The effect of increasing CMC concentration on the solubility of three drugs in aqueous 10% (w/v) HPβCD MS= 0.9 solution was also determined under the same condition as in Example 1. The results are shown in Table 2.

TABLE 2

The effect of increasing CMC concentration on solubilization.

| Drug | 0.00% CMC (w/v) | 0.10% CMC (w/v) | 0.25% CMC (w/v) | 0.50% CMC (w/v) |
|---|---|---|---|---|
| Acetazolamide | 2.52 | 3.60 | 3.21 | 3.75 |
| Hydrocortisone | 12.88 | 15.97 | 15.78 | 18.70 |
| Oxazepam | 0.90 | 1.49 | 1.31 | 1.88 |

EXAMPLE 3

The effect of heating on the solubilization of hydrocortisone in aqueous solution containing 10% (w/v) HPβCD MS= 0.6 and 0.25% (w/v) CMC was investigated as follows: An excess amount of hydrocortisone was added to the solution and the suspension which was formed was heated to 120° C. in a sealed container. The suspension was kept at this temperature for (a) 20, (b) 40, (c) 60 and (d) 80 minutes. At each time point, an aliquot of the suspension was removed and allowed to equilibrate for 3 days at room temperature (approximately 23 ° C.). After equilibration, each aliquot was filtered through a 0.45 μm membrane filter, diluted with a mixture of methanol and water (7:3 v/v) and analyzed by HPLC. The results in Table 3 show that the solubilizing effect of the HPβCD-CMC mixture increases with increasing duration of heating.

TABLE 3

The effect of heating on the solubilization of hydrocortisone.
The solubility of hydrocortisone in aqueous 10% (w/v)
HPβCD - 0.25% (w/v) CMC solution at room temperature.

| | Duration of Heating (Minutes) | | | |
|---|---|---|---|---|
| | 20 | 40 | 60 | 80 |
| Solubility (mg/ml) | 17.02 | 17.02 | 19.86 | 25.92 |

EXAMPLE 4

Part A

The effect of polyvinylpyrrolidone (PVP) of molecular weight 360,000 on drug-cyclodextrin complexation was investigated by determining the phase-solubility diagrams of hydrocortisone in aqueous 2-hydroxypropyl-β-cyclodextrin (HPβCD) of molar substitution (MS) 0.6 solutions and calculating the stability constant ($K_c$) for the complex from the slope and the solubility ($S_o$) of hydrocortisone in water ($1 \times 10^{-3}$ mol/liter).

$$K_c = \text{slope} \times (S_o \times (1-\text{slope}))^{-1}$$

An excess amount of the drug was added to water containing from 0 to 0.7% (w/v) PVP and varying amounts of HPβCD. The suspensions which formed were heated in sealed containers to 120° C. and kept at that temperature for 22 minutes. After equilibration for at least three days at room temperature (approximately 22° C.), aliquots of the suspensions were removed from the containers and each aliquot was filtered through a 0.45 μm membrane filter and analyzed by HPLC. The solubility of the drug was determined at least three times at each HPβCD and PVP concentration, and the slope of the phase-solubility diagram was determined by linear regression of the mean solubility versus HPβCD concentration values in mole per liter. The correlation coefficient (corr.) was calculated for each linear regression. The results are shown in Table A below.

TABLE A

The effect of PVP on the stability constant of the
hydrocortisone-HPβCD MS 0.6 complex at room temperature
(approx. 22° C.).

| PVP Concentration (% w/v) | Slope | Corr. | Kc (liter/mol) |
|---|---|---|---|
| 0 | 0.502 | 0.988 | 1010 |
| 0.01 | 0.528 | 0.972 | 1120 |
| 0.025 | 0.532 | 0.994 | 1140 |
| 0.05 | 0.544 | 0.977 | 1190 |
| 0.1 | 0.591 | 0.999 | 1450 |
| 0.15 | 0.577 | 0.999 | 1360 |
| 0.2 | 0.548 | 0.999 | 1210 |
| 0.3 | 0.535 | 0.995 | 1150 |
| 0.4 | 0.537 | 0.996 | 1160 |
| 0.5 | 0.544 | 0.998 | 1190 |
| 0.6 | 0.561 | 1.000 | 1280 |
| 0.7 | 0.543 | 0.999 | 1190 |

The results in Table A show that it was possible to obtain over 40% increase (at 0.1% PVP concentration) in $K_c$ by addition of PVP. The increase was concentration dependent and decreased somewhat upon further addition of PVP.

Part B

Comparable results were obtained when the effect of PVP on the solubilization of hydrocortisone by HPβCD MS 0.6 was investigated. The solubility of hydrocortisone was determined in aqueous 10% (w/v) HPβCD MS 0.6 solutions containing from 0 to 0.4% (w/v) PVP (molecular weight 360,000). An excess amount of hydrocortisone was added to the aqueous 10% HPβCD solutions and the suspensions which formed were heated in sealed containers to 120° C. and kept at that temperature for 22 minutes. After equilibration for at least three days at room temperature (approximately 22° C.), aliquots of the suspensions were removed from the containers and each aliquot was filtered through a 0.45 μm membrane filter and analyzed by HPLC. The solubility of the drug was determined at least three times at each PVP concentration and the results are shown in FIG. 1 (the mean values of three experiments ± the standard error of the mean).

FIG. 1 shows that a maximum solubilization of hydrocortisone in aqueous 10% (w/v) HPβCD MS 0.6 solution was obtained when 0.1 to 0.15% (w/v) PVP was present in the solution, and that the solubilization at the maximum was about 32% compared to aqueous 10% (w/v) HPβCD MS 0.6 solution containing no PVP. Similar results were obtained when other water-soluble polymers, e.g., carboxymethylcellulose and hydroxypropyl methylcellulose, were added to aqueous cyclodextrin solutions. Generally, a maximum solubilization was obtained when the polymer concentration was above 0.003% (w/v) but below 0.3%, but this was dependent on the type of polymer added to the aqueous cyclodextrin solution, the chain length (or the molecular weight) of the polymer and the cyclodextrin concentration in the aqueous solution.

The maximum effect is obtained at a very low polymer concentration before the polymer has any real effect on the viscosity of the solution. For example, the viscosity of a solution containing 10% or less PVP is essentially the same as that of water (*Handbook of Pharmaceutical Excipients*, American Pharmaceutical Association and the Pharmaceutical Society of Great Britain, Washington, 1986, pp. 234–239). Also, this increased solubilization (i.e., complexation) is a stable condition. The increased drug solubility frequently observed in viscous aqueous solutions, that is, formation of supersaturated drug solution, is an unstable condition which usually returns to a stable condition (under precipitation of the drug) within a few hours from its formation (Uekama et al., *J. Incl. Phenomena*, 1, 309–312, 1984). Thus, this increased complexation in the presence of a very small amount of a water-soluble polymer is not directly related to increased viscosity of the aqueous solution.

EXAMPLE 5

Solubilities (S) of three drugs in four different solvents, i.e., (a) water ($S_1$), (b) aqueous 0.25% (w/v) sodium carboxymethylcellulose solution (CMC) ($S_2$), (c) aqueous solution of 10% (w/v) hydroxyethyl-β-cyclodextrin (HEβCD) of molar substitution (MS)= 0.6 ($S_3$), and (d) aqueous solution containing both 0.25% (w/v) CMC and 10% (w/v) HEβCD MS= 0.6 ($S_4$), were determined as in Example 1. The results in Table 4 show that the solubilizing effect of HEβCD was increased by 32 to 53% ($S_4/S_3$=1.32 to 1.53) when 0.25% (w/v) CMC was present in the solution.

TABLE 4

The effect of CMC on the solubilization of drugs in aqueous HEβCD solutions.

| Drug | $S_1$ (mg/ml) | $S_2$ (mg/ml) | $S_3$ (mg/ml) | $S_4$ (mg/ml) | $S_4/S_3$ |
|---|---|---|---|---|---|
| Hydrocortisone | 0.36 | 1.10 | 17.51 | 26.81 | 1.53 |
| Miconazole | 0.04 | 0.06 | 2.51 | 3.31 | 1.32 |
| Sulfamethoxazole | 0.36 | 0.69 | 7.07 | 9.81 | 1.39 |

EXAMPLE 6

Solubilities (S) of hydrocortisone in four different solvents, i.e., (a) water ($S_1$), (b) aqueous 0.25% (w/v) hydroxypropyl methylcellulose solution (HPMC) ($S_2$), (c) aqueous solution of 5% (w/v) 2-hydroxypropyl-α-, β-, or γ-cyclodextrin (HPαCD, HPβCD, or HPγCD) of molar substitution (MS)= 0.6, 0.9 and 0.6, respectively, (S3), and (d) aqueous solution containing both 0.25% (w/v) HPMC and 5% (w/v) HPαCD, HPβCD, or HPγCD ($S_4$), were determined as in Example 1. The results in Table 5 show that the solubilizing effect of the cyclodextrin derivative was increased by 10 to 50% ($S_4/S_3$=1.1 to 1.5) when 0.25% HPMC was present in the solution.

TABLE 5

The effect of HPMC on the solubilization of hydrocortisone in aqueous cyclodextrin solutions.

| Cyclodextrin | $S_1$ (mg/ml) | $S_2$ (mg/ml) | $S_3$ (mg/ml) | $S_4$ (mg/ml) | $S_4/S_3$ |
|---|---|---|---|---|---|
| HPαCD MS = 0.6 | 0.4 | 1.4 | 2.4 | 3.6 | 1.5 |
| HPβCD MS = 0.9 | 0.4 | 1.4 | 6.7 | 7.7 | 1.2 |
| HPγCD MS = 0.6 | 0.4 | 1.4 | 7.7 | 8.7 | 1.1 |

EXAMPLE 7

Solubilities (S) of twelve drugs in four different solvents, i.e., (a) water ($S_1$), (b) aqueous 0.25% (w/v) polyvinylpyrrolidone solution (PVP) ($S_2$), (c) aqueous solution of 10% (w/v) hydroxypropyl-β-cyclodextrin (HPβCD) of molar substitution (MS)= 0.7 ($S_3$), and (d) aqueous solution containing both 0.25% (w/v) PVP and 10% (w/v) HPβCD MS= 0.7 ($S_4$), was determined as in Example 1. The results in Table 6 show that the solubilizing effect of HPβCD was increased by up to 129% ($S_4/S_3$= up to 2.29) when 0.25% (w/v) PVP was present in the solution.

TABLE 6

The effect of PVP on the solubilization of drugs in aqueous HPβCD solutions.

| Drug | $S_1$ (mg/ml) | $S_2$ (mg/ml) | $S_3$ (mg/ml) | $S_4$ (mg/ml) | $S_4/S_3$ |
|---|---|---|---|---|---|
| Acetazolamide | 0.70 | 1.05 | 2.80 | 3.66 | 1.31 |
| Carbamazepine | 0.11 | 0.31 | 6.43 | 7.50 | 1.17 |
| Clotrimazole | 0.00 | 0.00 | 1.20 | 1.80 | 1.50 |
| Dexamethasone | 0.26 | 0.33 | 7.53 | 8.00 | 1.06 |
| Econazole | 0.57 | 0.64 | 5.22 | 5.65 | 1.08 |
| 17β-Estradiol | 0.01 | — | 5.10 | 9.50 | 1.86 |
| Ethoxyzolamide | 0.04 | 0.06 | 1.36 | 2.72 | 2.00 |
| Miconazole | 0.04 | 0.20 | 2.36 | 3.40 | 1.44 |
| Progesterone | 0.00 | 0.00 | 4.76 | 5.71 | 1.20 |
| Oxazepam | 0.03 | 0.04 | 0.90 | 1.14 | 1.27 |
| Trimethoprim | 0.82 | 1.35 | 2.83 | 6.47 | 2.29 |
| Sulfamethoxazole | 0.36 | 0.86 | 5.71 | 8.92 | 1.56 |

EXAMPLE 8

Solubilities (S) of various drugs in eight different solvents, i.e., (a) water ($S_1$), (b) aqueous 10% (v/v) ethanol solution ($S_2$), (c) aqueous 0.25% (w/v) sodium carboxymethyl-cellulose solution (CMC) ($S_3$), (d) aqueous solution containing both 10% (v/v) ethanol and 0.25% (w/v) CMC ($S_4$), (e) aqueous solution of 10% (w/v) 2-hydroxypropyl-β-cyclodextrin (HPβCD) of molar substitution (MS)= 0.6 ($S_5$), (f) aqueous solution containing both 10% (v/v) ethanol and 10% (w/v) HPβCD MS= 0.6 ($S_6$), (g) aqueous solution containing both 0.25% (w/v) CMC and 10% (w/v) HPβCD MS= 0.6 ($S_7$), and (h) aqueous solution containing 10% (v/v) ethanol, 0.25% (w/v) CMC and 10% (w/v) HPβCD MS= 0.6 ($S_8$) were determined as in Example 1. The results in Table 7 show that CMC is also able to increase the solubilizing effect of HPβCD in aqueous ethanolic solutions.

TABLE 7

The effect of ethanol and CMC on the
solubilizing effect of HPβCD in aqueous solutions.

| Drug | Solubility (mg/ml) | | | | | | | |
| --- | --- | --- | --- | --- | --- | --- | --- | --- |
| | $S_1$ | $S_2$ | $S_3$ | $S_4$ | $S_5$ | $S_6$ | $S_7$ | $S_8$ |
| Acetazolamide | 0.70 | 1.11 | 0.84 | 0.75 | 2.52 | 2.19 | 3.11 | 2.50 |
| Hydrocortisone | 0.36 | 0.83 | 1.10 | 1.53 | 12.88 | 10.91 | 20.64 | 13.27 |
| Miconazole | 0.04 | 0.31 | 0.06 | — | 1.98 | 2.22 | 2.50 | 12.55 |

EXAMPLE 9

The permeability through a semi-permeable membrane was investigated. Semipermeable cellophane membrane was placed in a Franz diffusion cell containing 10 ml aqueous 5% (w/v) HPβCD solution as the receptor phase. The donor phase consisted of a suspension of approximately 3% (w/v) hydrocortisone in (a) aqueous 10% (w/v) hydroxypropyl-β-cyclodextrin (HPβCD) solution and (b) aqueous solution containing both 10% (w/v) HPβCD and 0.25% (w/v) carboxymethyl-cellulose (CMC), prepared as described in Example 1, and 2 ml of the donor phase applied to the membrane surface (area 3.1 cm$^2$). The assembled diffusion cells were kept at room temperature (22°+ 1° C.) and samples (30 µl) were removed from the donor phase every 10 minutes, up to 2 hours, and analyzed immediately by HPLC. The results shown in Table 8 clearly indicate that hydrocortisone is released faster from a suspension containing CMC than from suspension containing no CMC.

TABLE 8

The solubility (S) and the flux (F) of hydrocortisone
through a semi-permeable cellophane membrane
from hydrocortisone suspensions in HPβCD vehicles.

| Vehicle composition | S (mg/ml) | F (µg/cm$^2$/minute) |
| --- | --- | --- |
| Aqueous (10%) (w/v) HPβCD solution | 14.96 | 3.02 |
| Aqueous solution containing 10% (w/v) HPβCD and 0.25% (w/v) CMC | 19.23 | 5.36 |

EXAMPLE 10

The effect of carboxymethylcellulose (CMC) on the release of hydrocortisone from tablets containing hydrocortisone-HPβCD complex was investigated.

The freeze-dried hydrocortisone-HPβCD complex was prepared by adding an excess of hydrocortisone to aqueous solution containing 50% (w/w) (about 58% w/v) HPβCD and 0, 0.1 or 0.25% (w/v) CMC and heating the hydrocortisone suspensions formed for 20 minutes at 120° C. After equilibration for 3 days at room temperature, the suspensions were filtered through 0.45 µm membrane filters, the tiltrates were lyophilized and the solid which formed was ground with a mortar and pestle. The amount of hydrocortisone incorporated into the HPβCD complex was determined by HPLC.

Individual disks of 200 mg hydrocortisone-HPβCD complex were compressed in a hydraulic press under vacuum and a force of 1×10$^4$ kg for 1.5 minutes using a 13 mm (diameter) IR potassium bromide pellet punch. The disks had a cross-sectional area of 1.33 cm$^2$. Each disk contained approximately 27 mg of hydrocortisone.

The dissolution studies were carried out using a USP XXII described paddle apparatus for dissolution rate determination. The release rate was determined at 37±1° C. and 100 rpm by adding one tablet to 900 ml of water. Samples were withdrawn at various time intervals, filtered through 0.45 membrane filters and analyzed by HPLC.

Figure 2:
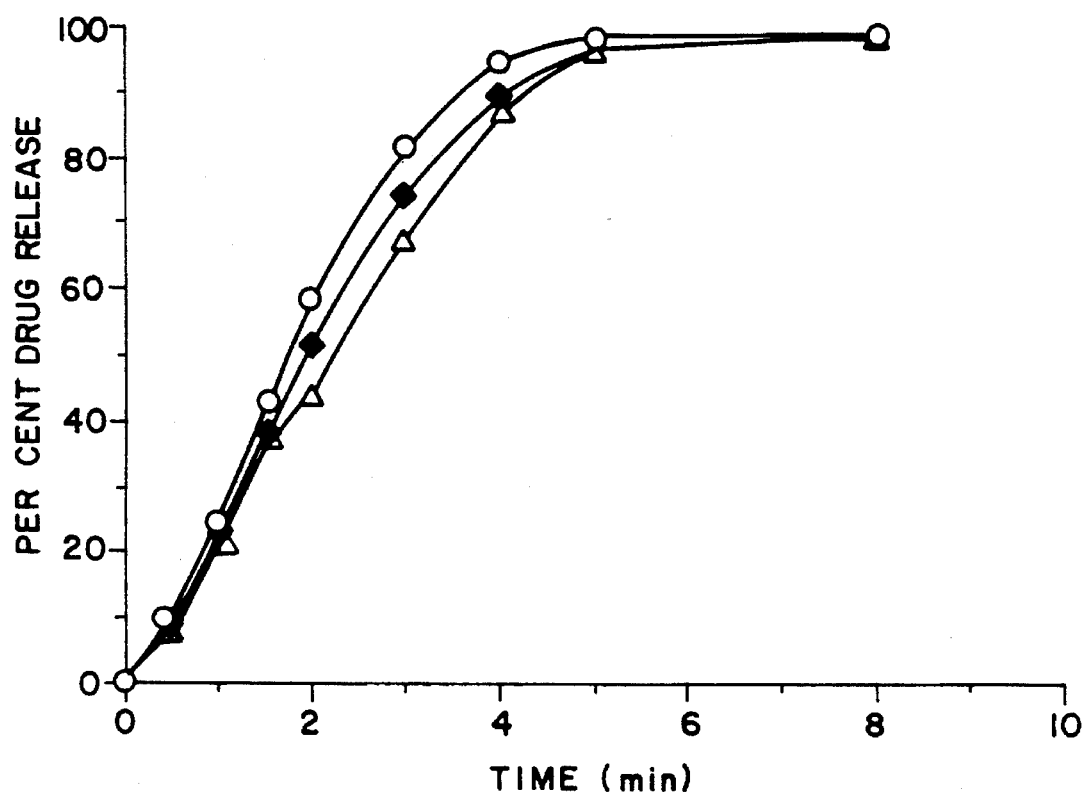
FIG. 2 is a series of plots depicting the dissolution profile of hydroconisone from tablets containing hydroconisone-HPβCD complex: Δ, 0% (w/v)CMC; ♦, 0.1% (w/v)CMC; o, 0.25% (w/v)CMC.

The results in FIG. 2 show that hydrocortisone dissolves significantly faster from tablets containing hydrocortisone-HPβCD complex prepared in the presence of CMC than from tablets prepared in the absence of CMC. The results shown in FIG. 2 are the average of four experiments. The dissolution tests were started at time zero. Three minutes later, 68.3% of the hydrocortisone had dissolved from tablets containing hydrocortisone-HPβCD complex formed without the addition of CMC, 74.2% of the hydrocortisone had dissolved from tablets containing hydrocortisone-HPβCD complex formed with the addition of 0.1% (w/v) CMC, and 81.0% of the hydrocortisone had dissolved from tablets containing hydrocortisone-HPβCD complex formed with the addition of 0.25% (w/v) CMC.

EXAMPLE 11

Eye drops containing a carbonic anhydrase inhibitor, acetazolamide, were prepared the following way: Hydroxypropyl methylcellulose (HPMC), 0.25% (w/v), was dissolved in distilled water and hydroxypropyl-β-cyclodextrin MS= 0.6, 20% (w/v), benzalkonium chloride [0.02% (w/v)] and the sodium salt of ethylenediaminetetraacetic acid [EDTA, 0.1% (w/v)] were then dissolved in the aqueous HPMC solution. Finally, acetazolamide, 1% (w/v), was added to this solution and dissolved by heating in an autoclave (120° C. for 20 min). The eye drop solution which formed was allowed to equilibrate at room temperature for one week.

Figure 3:
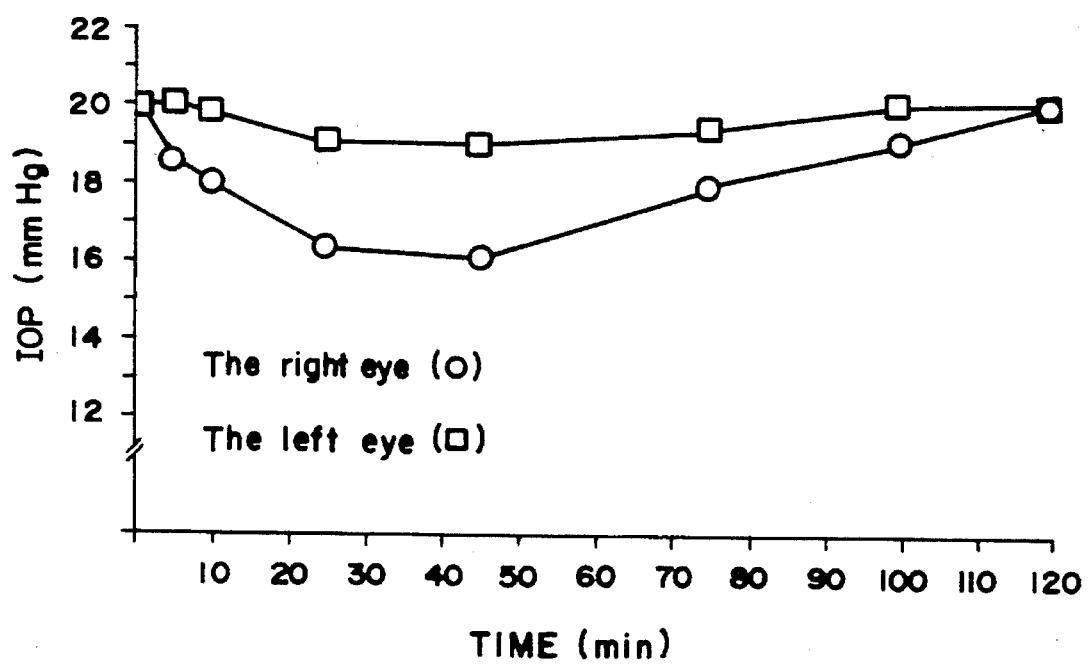
FIG. 3 is a pair of plotos illustrating the effect of 1% (w/v) acetazolamide eye drop solution on the intraocular pressure (IOP) of normotensive, conscious, albino rabbits, wherein the right eye received the drug (O) and the left eye was the control (□)

The topical activity of the carbonic anhydrase inhibitor eye drop solution was evaluated in conscious white New Zealand rabbits of either sex (2.5 to 3.5 kg). The intraocular pressure was recorded by a pneumatic tonometer without local anaesthesia. The eye drop solution (0.1 ml) was placed on the cornea of the right eye (the left eye was used as control) and the intraocular pressure was recorded at various time intervals (FIG. 3).

EXAMPLE 12

Hydrocortisone mouthwash was prepared in the following way: HPβCD MS= 0.6 (3.5% (w/v)), peppermint oil (0.05% (w/v)), ethanol (12% (v/v)), CMC (0.5% (w/v)), benzalkonium chloride (0.02% (w/v)) and the sodium salt of ethylenediaminetetraacetic acid (0.1% (w/v)) were dissolved in water and the solution was heated in a sealed container in an autoclave (120° C. for 20 minutes). After equilibration to room temperature, hydrocortisone (0.3% (w/v)) was dissolved in the cyclodextrin solution.

The topical activity of the hydrocortisone mouthwash solution was evaluated as follows: Patients were selected on the basis of severe ulceration, causing considerable pain, discomfort, inconvenience with work and the like. Normally the patients had unsuccessfully tried numerous other remedies such as gentian violet, chlorhexidine, silver nitrate, hydrocortisone, and triamcinolone, from a variety of sources. Each patient washed his/her mouth with 5–10 ml of the hydrocortisone mouthwash three to four times a day and the results were evaluated after treatment for two weeks. The results are shown in Table 9.

TABLE 9

Clinical results of treatment of patients with hydrocortisone mouthwash.

| Disease | Number of patients | | | | |
|---|---|---|---|---|---|
| | Total | Worse | No Change | Improved | Relapsed* |
| Lichen Planus | 17 | 1 | 2 | 14 | 1 |
| Recurrent oral ulceration | 6 | 0 | 0 | 6 | 1 |
| Miscellaneous autoimmune disease | 8 | 0 | 2 | 6 | 1 |

*Relapse, of those which showed improvement, within 6 months after end of treatment.

Quantitative Analysis

The quantitative determinations of the individual drugs were performed on a reversed-phase high-performance liquid chromatographic (HPLC) component system consisting of a Milton Roy ConstaMetric 3200 solvent delivery system, a Rheodyne 7125 injector, a Spectro Monitor 3200 uv/vis variable wavelength detector and a LiChrosorb®RP-18 5µ (125× 4 mm) column. For other conditions, see Table 10. The quantitative determination of econazole was done spectrophotometrically (Perkin-Elmer 550SE uv/vis spectrophotometer) at wavelength 225nm. Solvent ratios indicated refer to pans by volume.

TABLE 10

Conditions of quantitative drug determination by HPLC.

| Drug | Mobile phase | Flow rate (ml/min) | Wave length (nm) | Retention time (min) |
|---|---|---|---|---|
| Acetazolamide | Acetonitrile, acetic acid, water (10:2:88) containing 0.015% 1-octane-sulfonate | 1.5 | 263 | 4.0 |
| Alprazolam | Methanol, water (70:30) | 1.5 | 254 | 2.8 |
| Butylated hydroxyanisole | Methanol, water (70:30) | 1.5 | 285 | 3.6 |
| Camphor | Methanol, water (70:30) | 1.5 | 200 | 3.2 |
| Chlorbutol | Acetonitrile, water (60:40) | 1.5 | 205 | 2.0 |
| Dexamethasone | Acetonitrile, tetra-hydrofuran, water (30:5:65) | 1.5 | 254 | 4.0 |
| Diazepam | Methanol, water (75:25) | 1.5 | 226 | 4.0 |
| Ethoxyzolamide | Acetonitrile, water (35:65) containing 0.1% 1-hexane-sulfonate | 1.0 | 254 | 3.2 |
| Hydrocortisone | Acetonitrile, tetra-hydrofuran, water (30:1:69) | 1.5 | 254 | 2.6 |
| Methylparaben | Acetonitrile, water (36:64) | 1.5 | 260 | 4.4 |

TABLE 10-continued

Conditions of quantitative drug determination by HPLC.

| Drug | Mobile phase | Flow rate (ml/min) | Wave length (nm) | Retention time (min) |
|---|---|---|---|---|
| Methylyellow | Acetonitrile, water (78:22) | 1.5 | 205 | 5.2 |
| Miconazole | Methanol, 0.01M aqueous potassium phosphate solution (pH = 4.5) (90:10) | 1.5 | 272 | 2.6 |
| Oxazepam | Methanol, tetra-hydrofuran, water (55:2:43) | 1.5 | 226 | 2.8 |
| Pentachlorophenol | Acetonitrile, tetra-hydrofuran, water (78:3:19) | 1.5 | 248 | 2.4 |
| Prednisolone | Acetonitrile, acetic acid, water (17:0.5:82.5) | 1.5 | 242 | 4.0 |
| Propylparaben | Acetonitrile, water (40:60) | 1.5 | 260 | 5.2 |
| Salicylic acid | Methanol, acetic acid, water (35:1:64) | 1.5 | 300 | 4.8 |
| Sulfamethoxazole | Acetonitrile, acetic acid, water (30:1:69) | 1.5 | 253 | 2.4 |
| Temazepam | Methanol, water (70:30) | 1.5 | 275 | 2.8 |
| Triamcinolone acetonide | Acetonitrile, water (42:58) | 1.5 | 254 | 2.8 |
| Trimetoprim | Methanol, acetic acid, water (39:1:60) containing 0.005M 1-pentasulfonate | 1.5 | 287 | 2.4 |
| Vanillin | Methanol, water (70:30) | 1.5 | 275 | 2.4 |

EXAMPLE 13

To aqueous solutions containing 20% (w/v) 2-hydroxypropyl-β -cyclodextrin (HPβCD) of molar substitution (MS)= 0.6 were added 0.25% (w/v) polyvinylpyrrolidone (PVP), 0.25% (w/v) sodium carboxymethylcellulose (CMC) or 0.25% (w/v) hydroxypropyl methylcellulose (HPMC). The resultant solutions were heated in sealed containers to 120° C. and maintained at that temperature for 30 minutes, then were lyophilized. The solids thus obtained were ground with a mortar and pestle.

The solid cyclodextrin/polymer products were reconstituted with water to afford solutions containing 9.88% (w/v) HPβCD and 0.12% (w/v) PVP, 0.12% (w/v) or CMC 0.12% (w/v) HPMC. The solubilities (S) of three drugs in these solutions and in an aqueous solution containing 10% (w/v) HPβCD without added polymer were then determined as follows:

An excess amount of each drug was added to each of the four cyclodextrin solutions and the solutions were sonicated in an ultrasonic bath for 3 hours, then allowed to equilibrate for 60 hours at room temperature (23° C.). After equilibration, aliquots were filtered through 0.45 mm membrane filters, diluted with a mixture of methanol and water and analyzed by an HPLC method. The results are set forth in Table 11 below, where $S_1$ is the solubility in aqueous solution containing 10% (w/v) HPβCD; $S_2$ is the solubility in aqueous solution containing 9.88% (w/v) HPβCD and 0.12% (w/v) PVP; $S_3$ is the solubility in aqueous solution containing 9.88% (w/v) HPβCD and 0.12% (w/v) CMC; and $S_4$ is the solubility in aqueous solution containing 9.88% (w/v) HPβCD and 0.12% (w/v) HPMC. The results show that a solid polymer/cyclodextrin product can be prepared which has enhanced complexing abilities, and that the drug itself need not be heated to achieve enhancement. Nevertheless, it is expected that a greater increase in solubility would be observed at higher polymer concentrations [e.g., 0.25% (w/v)], and/or if the solutions were heated after addition of the drug. However, by separate preparation of the cyclodextrin/polymer complexing agent as illustrated here, one can readily avoid heating drugs which are unstable at elevated temperature.

TABLE 11

The effect of previously prepared solid HPβCD-polymer complexing agent mixture on the solubility of drugs.
Solution $S_1$ contained 10% (w/v) HPβCD.
Solutions $S_2$, $S_3$ and $S_4$ contained 9.88% (w/v) HPβCD and 0.12% (w/v) of the polymer.

| Drug | $S_1$ (mg/ml) | $S_2$ (mg/ml) | $S_3$ (mg/ml) | $S_4$ (mg/ml) |
|---|---|---|---|---|
| Carbamazepine | 7.00 | 9.80 | 6.66 | 9.53 |
| Econazole | 4.86 | 5.57 | 5.20 | 6.32 |
| Hydrocortisone | 12.88 | 16.47 | 14.52 | 16.05 | tion ($S_3$), d) aqueous 0.25% (w/v) hydroxypropyl methylcellulose (HPMC) solution ($S_4$), e) aqueous solution of 10% (w/v) 2-hydroxypropyl-β-cyclodextrin (HPβCD) of molar substitution (MS)= 0.6 ($S_5$), f) aqueous solutions containing both 0.25% (w/v) CMC and 10% (w/v) HPβCD MS= 0.6 ($S_6$), g) aqueous solutions containing both 0.25% (w/v) PVP and 10% (w/v) HPβCD MS= 0.6 ($S_7$), and h) aqueous solutions containing both 0.25% (w/v) HPMC and 10% (w/v) HPβCD MS= 0.6 ($S_8$). An excess amount of the compound to be tested was added to each solvent and the suspensions which formed were heated in sealed containers to 120° C. The solubility of salicylic acid was determined in acidic (HCl) solution. The suspensions were kept at this temperature for 20 minutes and then allowed to equilibrate for 3 days at room temperature (approximately 23° C.). After equilibration, aliquots were filtered through 0.45 μm membrane filters, diluted with a mixture of methanol and water (7:3) and analyzed by a high pressure liquid chromatographic (HPLC) method. The results in Table 12 show that the solubilizing effect of HPβCD was increased by 2 to 134% (solubility ratio of 1.02 to 2.34) when 0.25% polymer (CMC, PVP or HPMC) was present in the solution.

EXAMPLE 14

Solubilities (S) of various compounds were determined in eight different solvents, i.e., a) water ($S_1$), b) aqueous 0.25%

TABLE 12

The effect of polymers on the solubilization of various compounds in aqueous HPβCD solutions.
The solubility ratios (the solubility in HPβCD solution containing the polymer divided by the solubility in HPβCD solution containing no polymer) are shown in parentheses.

| Compound | $S_1$ (mg/ml) | $S_2$ (mg/ml) | $S_3$ (mg/ml) | $S_4$ (mg/ml) | $S_5$ (mg/ml) | $S_6$ (mg/ml) | $S_7$ (mg/ml) | $S_8$ (mg/ml) |
|---|---|---|---|---|---|---|---|---|
| Butylated hydroxyanisole | 0.40 | 0.40 | 1.24 | 0.28 | 13.9 | 14.3 (1.03) | 15.8 (1.14) | 15.5 (1.12) |
| Camphor | 1.84 | 2.01 | 2.20 | 1.92 | 12.7 | 13.8 (1.09) | 13.7 (1.08) | 13.3 (1.05) |
| Chlorbutol | 8.11 | 8.41 | 8.41 | 8.15 | 28.6 | 29.3 (1.02) | — | 29.9 (1.05) |
| Cholecalciferol | NO | NO | NO | NO | 0.61 | 0.72 (1.18) | 0.76 (1.25) | 0.69 (1.14) |
| Methylparaben | 3.16 | 3.16 | 3.40 | 3.16 | 8.46 | — | 10.5 (1.24) | 11.4 (1.35) |
| Methylyellow | $6.4 \times 10^{-4}$ | $8.5 \times 10^{-4}$ | $8.5 \times 10^{-4}$ | $7.5 \times 10^{-4}$ | 0.23 | 0.24 (1.04) | 0.24 (1.04) | 0.25 (1.09) |
| Pentachlorophenol | 0.02 | 0.06 | 0.03 | 0.03 | 0.61 | 0.99 (1.62) | 1.43 (2.34) | — |
| Propylparaben | 0.19 | 0.33 | 0.29 | 0.29 | 8.28 | 8.90 (1.07) | 9.00 (1.09) | 8.85 (1.07) |
| Salicylic acid | — | — | — | — | 3.71 | 4.23 (1.14) | 4.07 (1.10) | 3.92 (1.06) |
| Vanillin | 13.9 | 13.7 | 11.5 | 17.1 | 25.0 | 27.3 (1.09) | — | 26.5 (1.06) |

—: Not tested.
NO: No solubility could be observed, the solubility was below the detection limits.

(w/v) sodium carboxymethylcellulose (CMC) solution ($S_2$), c) aqueous 0.25% (w/v) polyvinylpyrrolidone (PVP) solu-

EXAMPLE 15

The effect of polyvinylpyrrolidone (PVP) on transdermal delivery of hydrocortisone from aqueous 2-hydroxypropyl-β-cyclodextrin of molar substitution 0.6 (HPβCD MS 0.6) was investigated in vitro. Female hairless mice were sacrificed by cervical dislocation. The whole dorsal skin was removed and placed carefully in a Franz diffusion cell containing 10 ml aqueous 5% (w/v) HPβCD MS 0.6 as the receptor phase. The donor phase consisted of a saturated hydrocortisone solution in (a) aqueous 8% (w/v) HPβCD MS 0.6 solution and (b) aqueous solution containing both 6% (w/v) HPβCD MS 0.6 and 0.25% (w/v) PVP, prepared as described in Example 1. [The amounts of cyclodextrin and polymer were selected such that solutions (a) and (b) achieved equivalent solubilizing of the drug.]. Two ml of the donor phase were applied to the skin surface (area 3.1 cm$^2$). The diffusion cells were kept at constant temperature by circulating 37° C. water from a constant temperature water bath and samples (500 μm) were removed at various time intervals, up to three days, from the donor phase and analyzed by HPLC. The results in Table 13 clearly show that transdermal delivery of hydrocortisone was over two times faster from the PVP-containing sample.

TABLE 13

The concentration of a saturated solution (C) and the flux (F) of hydrocortisone through hairless mouse skin from HPβCS MS 0.6 containing vehicles. Each experiment was repeated 4 times and the results are the mean ± standard deviation.

| Vehicle composition | C (mg/ml) | F (μm/cm$^2$/h) |
|---|---|---|
| Aqueous 8% (w/v) HPβCD MS 0.6 solution | 10.9 | 0.075 ± 0.023 |
| Aqueous solution containing both 6% (w/v) HPβCD MS 0.6 and 0.25% (w/v) PVP | 10.6 | 0.158 ± 0.035 |

EXAMPLE 15a

Figure 4:
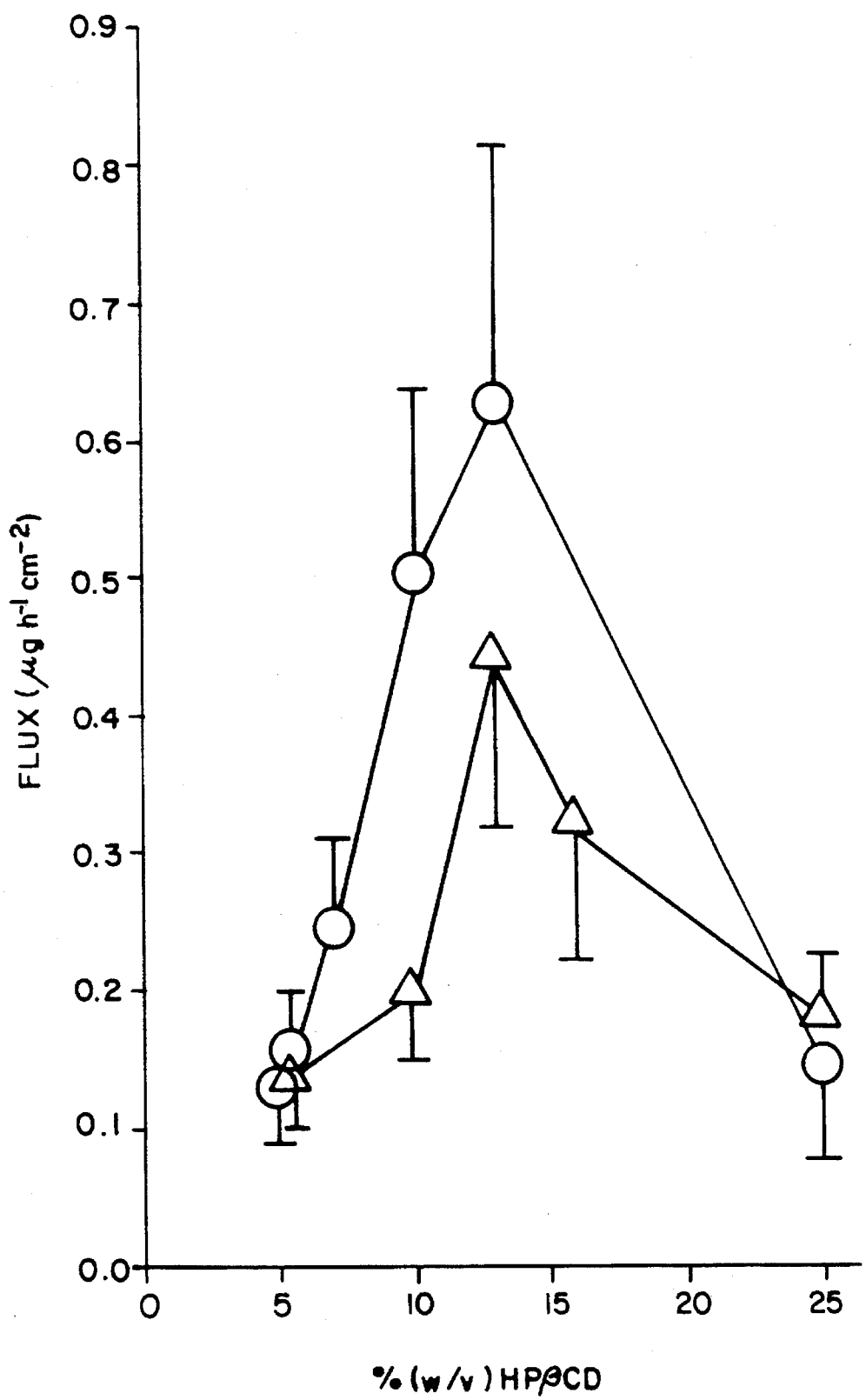
FIG. 4 is a pair of plots illustrating the effect of HPβCD concentration on the flux of hydroconisone through hairless mouse skin in vivo for aqueous HPβCD solutions (Δ) and aqueous HPβCD solutions containing 0.25% (w/v) PVP (O)

The effect of polyvinylpyrrolidone (PVP) on transdermal delivery of hydrocortisone from aqueous 2-hydroxypropyl-β-cyclodextrin of molar substitution 0.6 (HPβCD) solution was investigated in vitro. Female hairless mice were sacrificed by cervical dislocation and their full-thickness skins were removed and placed in Franz diffusion cells of type FDC 400 15FF, diameter 1.5 cm (Vangard International Inc., USA), containing 12.3 ml receptor phase. The receptor phase consisted of phosphate buffer saline pH 7.4 containing 0.3% (w/v) Brij-58™ and 0.4% (v/v) formaldehyde and was stirred with a magnetic bar. The receptor chamber was kept at 37° C. by circulating water through an external jacket. The donor phase consisted of 1.6% (w/v) suspension or solution of hydrocortisone in an aqueous HPβCD solution or an aqueous HPβCD solution containing 0.25% (w/v) PVP, which has been treated in an autoclave (120° C. for 20 min). After equilibration for three days, 2.0 ml of the donor phase was applied to the skin surface (the stratum corneum) and the donor chamber covered with Parafilm™ (a paraffin-coated plastic film). Samples of the receptor phase were removed from the cells, at 12 hour intervals, for three days and replaced with fresh buffer solution. The samples were kept frozen until analyzed by HPLC. Each experiment was repeated at least three times. The results depicted in FIG. 4 are the mean values ± standard error of the mean (SE).

PVP had a small but notable effect on the viscosity (measured in a Brookfield digital viscometer). At room temperature, the viscosity of the aqueous 10% (w/v) HPβCD solution was 1.5 mPa's increasing to 2.2 mPa's when 0.25% (w/v) PVP was added to the solution. It is highly unlikely that this small viscosity increase had any significant effect on the release of hydrocortisone from the aqueous HPβCD-containing vehicle. On the other hand, addition of a small amount of PVP to the aqueous complexation medium significantly increased the stability of the hydrocortisone-HPβCD complex, as shown in Example 4 hereinabove. The apparent stability constant of the hydrocortisone-HPβCD complex was determined to be $1.0 \times 10^3 M^{-1}$ when no polymer was present in the aqueous HPβCD solution, but $1.5 \times 10^3 M^{-1}$ when 0.25% (w/v) PVP was present. Thus, addition of a small amount of PVP to the aqueous complexation medium significantly increased the stability of the hydrocortisone-HPβCD complex, resulting in a 30% increase in solubilization of the drug in 10% (w/v) HPβCD solution. See FIG. 1 and Example 4B.

In the skin permeability studies, the HPβCD concentration varied from 5 to 25% (w/v). Initially, when hydrocortisone was in suspension, the flux was increased upon increased HPβCD concentration, as shown in FIG. 4. When all the hydrocortisone was in solution, at a HPβCD concentration between 10 and 13% (w/v), increased HPβCD concentration resulted in flux decrease. When the hydrocortisone was in suspension, increasing the HPβCD concentration increased the amount of dissolved hydrocortisone and, since the rate of hydrocortisone release from the hydrocortisone-HPβCD complex was much faster than the rate of hydrocortisone dissolution, this consequently led to greater flux through the skin. On the other hand, when all the hydrocortisone was in solution, increasing the HPβCD concentration led to increased complexation of hydrocortisone and, since the hydrated hydrocortisone-HPβCD complex only permeates the skin with great difficulty, this led to a decreased flux through the skin. The proposed mechanism is shown in FIG. 5.

Figure 5:
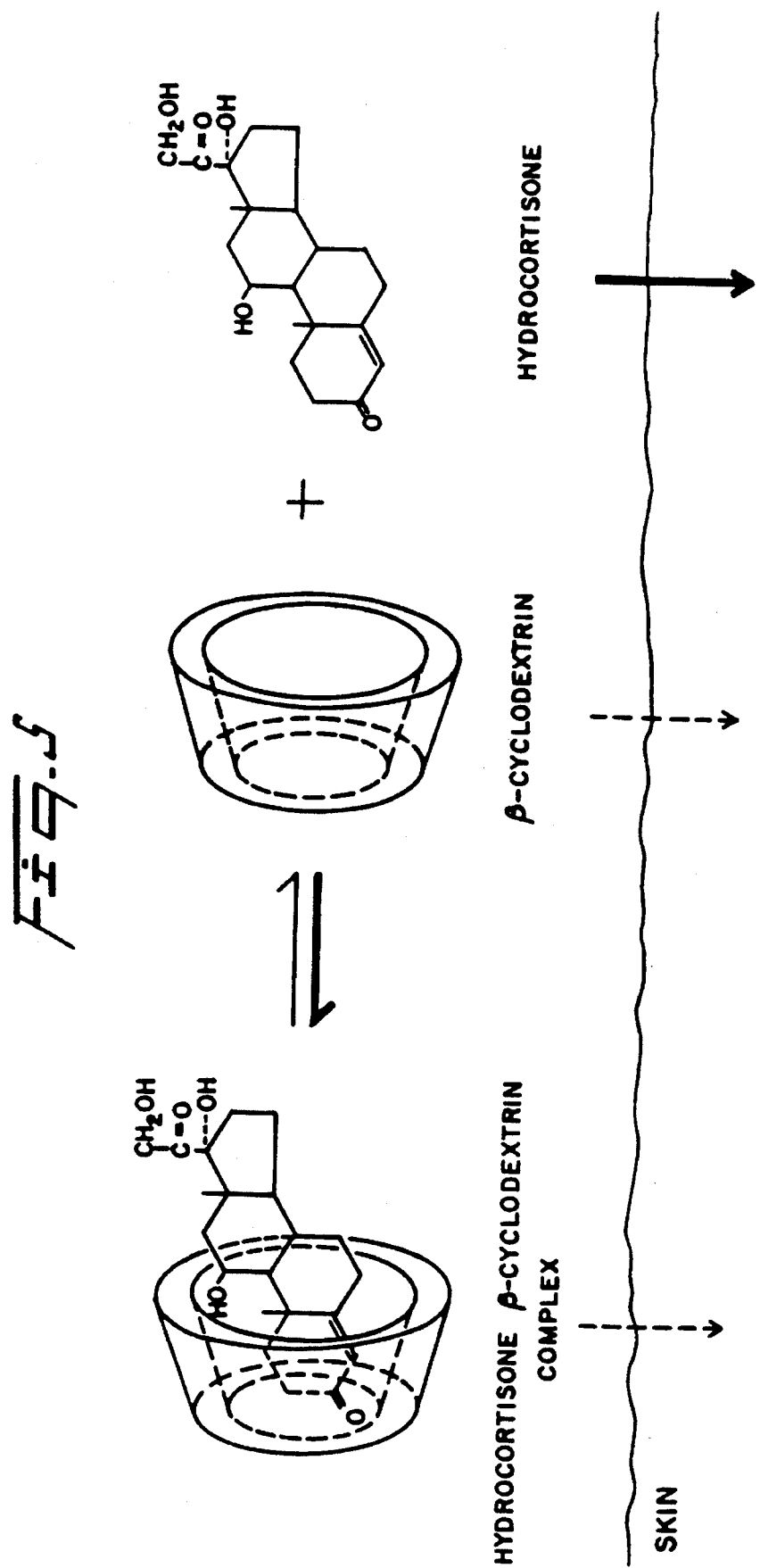
FIG. 5 is a diagrammatic representation of the effect of HPβCD on the transdermal delivery of hydrocortisone, illustrating that due to its size and hydrophilicity, the HPβCD molecule only permeates the skin with great difficulty.

When the stability of the hydrocortisone-HPβCD complex was increased by addition of PVP, then the equilibrium in FIG. 5 was pushed to left. When the (drug-HPβCD)-PVP containing aqueous vehicle came in contact with the skin surface, PVP was adsorbed to the surface. When PVP was adsorbed to the skin surface then, in the micro-environment close to the skin surface, the stability constant of the complex decreased from $1.5 \times 10^3 M^{-1}$ to $1.0 \times 10^3 M^{-1}$, or about 33%. Then the equilibrium in FIG. 5 was shifted toward the right, the hydrocortisone molecules were released from the HPβCD complex and a supersaturated drug solution was formed at the skin surface. The free hydrocortisone molecules then partitioned into and then penetrated through the skin. At its maximum (HPβCD concentration about 12% w/v), the flux of hydrocortisone was about 40% larger when 0.25% (w/v) PVP was present in the HPβCD containing vehicle than when no PVP was present. A similar mechanism is proposed for the transcorneal delivery of dexamethasone, as described in Example 18 hereinbelow.

EXAMPLE 16

Solubilities (S) of hydrocortisone and carbamazepine in aqueous solutions containing various cyclodextrins (CDs), i.e., γ-cyclodextrin (γCD), hydroxyethyl-β-cyclodextrin (HBβCD) with molar substitution (MS) 0.6, methyl-β-cyclodextrin (MβCD) with degree of substitution 1.8, monosubstituted glucosyl-α-cyclodextrin (Glucosyl-αCD), monosubstituted glucosyl-β-cyclodextrin (Glucosyl-βCD), monosubstituted maltosyl-α-cyclodextrin (Maltosyl-αCD), or monosubstituted maltosyl-β-cyclodextrin (Maltosyl-βCD), with and without 0.25% (w/v) polymer, i.e., sodium carboxymethylcellulose (CMC), polyvinylpyrrolidone (PVP) or hydroxypropyl methylcellulose (HPMC), were determined as in Example 1. The results in Table 14 show that the polymers increased the solubilizing effect of the CD derivatives by 8 to 156% ($S_{cp}/S_{co}$=1.08 to 2.56) when 0.25% polymer was present in the solution.

TABLE 14

The effect of polymers on the solubilization of hydrocortisone and carbamazepine in aqueous CD solutions.

| Cyclodextrin | Polymer | $S_{co}{}^a$ (mg/ml) | $S_{cp}{}^b$ (mg/ml) | $S_{cp}/S_{co}{}^c$ |
|---|---|---|---|---|
| Carbamazepine: | | | | |
| γCD | CMC | 0.49 | 0.65 | 1.33 |
| γCD | PVP | 0.49 | 1.07 | 2.18 |
| γCD | HPMC | 0.49 | 1.11 | 2.27 |
| Hydrocortisone: | | | | |
| γCD | CMC | 3.22 | 4.32 | 1.34 |
| γCD | PVP | 3.22 | 4.81 | 1.49 |
| γCD | HPMC | 3.22 | 8.23 | 2.56 |
| HEβCD | CMC | 17.5 | 26.8 | 1.53 |
| MβCD | CMC | 18.6 | 20.1 | 1.08 |
| MβCD | PVP | 18.6 | 20.2 | 1.09 |
| MβCD | HPMC | 18.6 | 21.8 | 1.17 |
| Glucosyl-αCD | CMC | 2.7 | 5.4 | 2.00 |
| Glucosyl-αCD | PVP | 2.7 | 3.6 | 1.33 |
| Glucosyl-αCD | HPMC | 2.7 | 5.4 | 2.00 |
| Glucosyl-βCD | CMC | 17.0 | 20.2 | 1.19 |
| Glucosyl-βCD | PVP | 17.0 | 22.2 | 1.31 |
| Maltosyl-αCD | CMC | 4.1 | 6.1 | 1.49 |
| Maltosyl-βCD | CMC | 10.4 | 18.3 | 1.76 |
| Maltosyl-βCD | PVP | 10.4 | 19.5 | 1.88 |
| Maltosyl-βCD | HPMC | 10.4 | 17.9 | 1.72 |

$a$ = Solubility of hydrocortisone in aqueous 10% (w/v) CD solution; solubility of carbamazepine in aqueous 5% (w/v) CD solution.
$b$ = Solubility in aqueous solution containing both 0.25% (w/v) of the given polymer and either 10% (w/v) CD in the case of hydrocortisone or 5% (w/v) CD in the case of carbamazepine.
$c$ = The solubility ratio.

EXAMPLE 17

The effect of polyvinylpyrrolidone (PVP) on the enthalpy (ΔH) and the entropy (ΔS) of the stability constant ($K_c$) of the drug-cyclodextrin complex was determined. The phase-solubility diagrams of hydrocortisone, 17β-estradiol and acetazolamide in aqueous 2-hydroxypropyl-β-cyclodextrin (HPβCD) of molar substitution (MS) 0.6, or aqueous 2-hydroxypropyl-α-cyclodextrin (HPαCD) MS 0.6 solutions, containing from 0 to 0.5% (w/v) PVP, were determined and the stability constant ($K_c$) was calculated for the complex from the slope (see Example 4).

An excess amount of the drug was added to water containing 0, 0.1, 0.25 or 0.5% (w/v) PVP and various amounts of HPβCD or HPαCD. The suspensions which formed were heated in sealed containers to 120° C. and kept at that temperature for 22 minutes. After equilibration for at least seven days at 6°, 20°, 30°, 40° and 50° C., aliquots of the suspensions were removed from the containers and each aliquot was filtered through a 0.45 μm membrane filter and analyzed by HPLC. $K_c$ was calculated at each temperature and ΔH and ΔS were calculated as described in A. Martin, J. Swarbrick and A. Cammarata: *Physical Pharmacy: The Physical Chemical Principles in the Pharmaceutical Sciences,* Third Edition, Lea & Febiger, Philadelphia, 1983, Chapter 13, pp. 314–348.

The results are shown in Tables 15–19 below.

TABLE 15

The effect of PVP on ΔH and ΔS for the stability constant ($K_c$) of the acetazolamide-HPβCD MS 0.6 complex.

| PVP concentration (% w/v) | ΔH (kJ mol$^{-1}$) | ΔS (J mol$^{-1}$K$^{-1}$) |
|---|---|---|
| 0.00 | −18.4 | −26.0 |
| 0.10 | −25.8 | −49.6 |
| 0.25 | −24.8 | −46.2 |
| 0.50 | −25.8 | −49.8 |

TABLE 16

The effect of PVP on ΔH and ΔS for the stability constant ($K_c$) of the hydrocortisone-HPαCD MS 0.6 complex.

| PVP concentration (% w/v) | ΔH (kJ mol$^{-1}$) | ΔS (J mol$^{-1}$K$^{-1}$) |
|---|---|---|
| 0.00 | −32.1 | −70.2 |
| 0.10 | −39.3 | −94.5 |
| 0.25 | −48.4 | −124.2 |
| 0.50 | −35.7 | −81.9 |

TABLE 17

The effect of PVP on ΔH and ΔS for the stability constant ($K_c$) of the hydrocortisone-HPβCD MS 0.6 complex.

| PVP concentration (% w/v) | ΔH (kJ mol$^{-1}$) | ΔS (J mol$^{-1}$K$^{-1}$) |
|---|---|---|
| 0.00 | −20.4 | −6.2 |
| 0.10 | −41.0 | −68.6 |
| 0.25 | −36.5 | −56.4 |
| 0.50 | −38.8 | −64.9 |

TABLE 18

The effect of PVP on ΔH and ΔS for the stability constant ($K_c$) of the 17β-estradiol-HPβCD MS 0.6 complex.

| PVP concentration (% w/v) | ΔH (kJ mol$^{-1}$) | ΔS (J mol$^{-1}$K$^{-1}$) |
|---|---|---|
| 0.00 | −71.1 | −151 |
| 0.10 | −75.3 | −166 |
| 0.25 | −89.5 | −213 |
| 0.50 | −81.2 | −185 |

It has been shown that ΔH and ΔS generally become more negative as the stability constant for molecular complexation increases (A. Martin, J. Swarbrick and A. Cammarata: *Physical Pharmacy: The Physical Chemical Principles in the Pharmaceutical Sciences,* Third Edition, Lea & Febiger, Philadelphia, 1983, Chapter 13, pp. 314–348). As the binding between the drug and the cyclodextrin becomes stronger, ΔH would be expected to have a larger negative value. Apparently, PVP increases the structural restraint of the complex in the aqueous solution, leading to a larger negative ΔS value. These thermodynamic changes indicate that the water-soluble PVP polymer participates directly in the complex formation.

TABLE 19

The effect of PVP on the apparent
stability constant of the drug-
cyclodextrin complexes at 20° C.

| | | Apparent stability constant ($M^{-1}$) | |
|---|---|---|---|
| Drug | Cyclodextrin | 0.00% (w/v) PVP | 0.25% (w/v) PVP |
| Acetazolamide | HPβCD | 86 | 97 |
| Hydrocortisone | HPαCD | 112 | 124 |
| 17β-Estradiol | HPβCD | 53000 | 78000 |

HPαCD = hydroxypropyl-α-cyclodextrin
HPβCD = hydroxypropyl-β-cyclodextrin

EXAMPLE 18

The effect of hydroxypropyl methylcellulose (HPMC) on the transcorneal delivery of dexamethasone was investigated in vivo in humans. Patients were administered a single drop of dexamethasone eye drop solution containing 0.67% dexamethasone in 2-hydroxypropyl-β -cyclodextrin of molar substitution 0.6 (HPβCD) and 0.25% HPMC isotonic (NaCl) water solution, three hours before cataract surgery. The HPβCD concentration was kept at 10% above the saturation concentration. That is, 10% more cyclodextrin than was needed to dissolve all dexamethasone in the aqueous eye drop solution was used. This was done to prevent eventual precipitation during storage and temperature fluctuations. One solution was heated in an autoclave (120° C. for 20 minutes), the other was filtered through a 0.22 μm membrane filter. For comparison, transcorneal delivery of dexamethasone from Maxidex®, which contains 0.1% dexamethasone in an aqueous suspension, was also determined. During the operation, 0.1 ml of the aqueous humor was aspirated from the anterior chamber, and the dexamethasone concentration was determined by HPLC.

The intraocular dexamethasone concentration was 164±37 ng/ml after administration of the 0.67% dexamethasone-HPβCD eye drops which had been heated, compared to 49±0.15 ng/ml after administration of the 0.67% dexamethasone-HPβCD eye drops which had only been filtered and 20±13 ng/ml after administration of Maxidex® (mean±standard error, n=5). No toxic effects were observed. These results show that heating (i.e., formation of the polymer/cyclodextrin co-complex) significantly enhances the transcorneal delivery of dexamethasone. The mechanism of the enhancement is explained in Example 15a hereinabove.

The foregoing Examples provide evidence of the formation of a polymer/cyclodextrin/drug co-complex herein. Example 13 shows that the HPβCD-polymer complexing agent has greater solubilizing/complexing power than the cyclodextrin alone. Various other facts support the conclusion that a co-complex is formed, for example:

(1) The various solubility studies indicate that the solubilizing effect of cyclodextrin is increased when water-soluble polymer is added to the aqueous cyclodextrin solution in accord with the present invention. The effect is shown to be synergistic, which indicates direct involvement of the polymer in the drug-cyclodextrin complexation. If the polymer and cyclodextrin acted as independent complexing agents, the effect would only be additive, while in fact a much greater effect is obtained.

(2) The apparent stability constants of the drug -cyclodextrin complexes were increased when the polymers were present in the aqueous cyclodextrin complexation media in accord with the present invention. Thus, the apparent stability constant of a hydrocortisone-HPβCD complex was increased from about $1000M^{-1}$ to about $1500M^{-1}$, or about 50%, when a small amount of PVP was added to the complexation medium; see Example 4A and Table A. In Table 19, it is shown that the apparent stability constant of an acetazolamide-HPβCD complex was increased 13%, that of a hydrocortisone-HPαCD complex was increased 11% and that of a 17β-estradiol-HPβCD complex was increased 47% when 0.25% PVP (w/v) was present in the complexation medium. Similarly, it has been found in other studies that the apparent stability constant of a dexamethasone-HPβCD complex was increased from $1230M^{-1}$ to $1550M^{-1}$ (about 26%) when hydroxypropyl methylcellulose was present in the complexation medium. These increases in apparent stability constants and the substantial changes in both enthalpy and entropy can only be explained by direct involvement of the polymer in the complexation.

(3) The formation of a co-complex of cyclodextrin, drug and polymer in accord with the present invention is also supported by the results of studies of permeability through the skin (Examples 15 and 15a), through the cornea of the eye (Example 18) and through a semi-permeable cellophane membrane. These studies show that when the drug forms a suspension in the donor phase (i.e., the vehicle), the flux of the drug increases faster upon increased cyclodextrin concentration when the polymer is present than when it is absent. If all of the drug is in solution, the flux decreases faster upon increased cyclodextrin concentration when the polymer is present than when it is absent. At the maximum of the permeability profiles, the double character of the (drug-cyclodextrin)polymer co-complexes ensures greater flux of the drug through the membrane from the drug-cyclodextrin-polymer co-complexes than from simple drug-cyclodextrin complexes. This is explained in Example 15a.

(4) The formation of a co-complex, as a "string of pearls" or "water droplets on a spider's web", is supported by the results of other investigators on the effect of water soluble polymers on the solubilizing effects of micelies, discussed in detail above.

(5) Previous investigations of the effects of cyclodextrins on proteins have shown that cyclodextrins enhance the solubilization and stabilization of proteins, indicating a form of complex formation. See Loftsson et al, *Pharm. Ztg. Wiss.* 4/136, 5–10 (1991) and European Patent Publication No. 0437478. The improvements in cyclodextrin's solubilization and stabilization of drugs observed herein when polymers (which, like proteins, are macromolecules) are heated therewith lead to the conclusion that a similar form of complex formation to that observed with proteins is involved here. While cyclodextrins form inclusion complexes with non-macromolecular drugs, i.e. the drug molecule or a portion thereof is encapsulated within the cavity of the cyclodextrin molecule, a different sort of complexation is predicated is the case of macromolecules. The fact that use of the polymer in accord with the present invention has been found to enhance rather than compete with drug-cyclodextrin complexation is also evidence that the son of complexation which occurs in the case of the polymers is different from the usual inclusion complexation of non-macromolecular drugs.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A method for enhancing the complexation of cyclodextrin with a lipophilic and/or water-labile active ingredient which is a drug, cosmetic additive, food additive or agrochemical, said method comprising combining from about 0.1 to about 70% (weight/volume) of cyclodextrin, from about 0.001 to about 5% (weight/volume) of a pharmacologically inactive water-soluble polymer acceptable for use in a pharmaceutical, cosmetic, food or agricultural composition, and said lipophilic and/or water-labile active ingredient in an aqueous medium, the polymer and cyclodextrin being dissolved in the aqueous medium before the active ingredient is added, the aqueous medium which comprises the polymer and cyclodextrin being maintained at from about 30° to about 150° C. for a period of from about 0.1 to about 100 hours before, during and/or after the active ingredient is added, optionally followed by removal of water.

2. The method according to claim 1, wherein the aqueous medium is maintained at from about 30° to about 150° C. for from about 0.1 to about 100 hours before the active ingredient is added.

3. The method according to claim 1, wherein the aqueous medium is maintained at from about 30° to about 150° C. for from about 0.1 to about 100 hours after the active ingredient is added.

4. The method according to claim 1, wherein the amount of water-soluble polymer is from about 0.01 to about 0.5% (weight/volume).

5. The method according to claim 1, wherein the cyclodextrin comprises at least one member selected from the group consisting of α-, β- and γ-cyclodextrhn and the hydroxypropyl, hydroxyethyl, dihydroxypropyl, glucosyl and maltosyl derivatives of α-, β- and γ-cyclodextrin having a molar degree of substitution of from about 0.05 to about 10.

6. The method according to claim 1, wherein the pharmacologically inactive water-soluble polymer is a cellulose derivative.

7. The method according to claim 6, wherein the cellulose derivative is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethyl cellulose or sodium carboxymethylcellulose.

8. The method according to claim 7, wherein the cellulose derivative is hydroxypropyl methylcellulose.

9. The method according to claim 7, wherein the cellulose derivative is sodium carboxymethylcellulose.

10. The method according to claim 1, wherein the pharmacologically inactive water-soluble polymer is a natural polysaccharide or polypeptide.

11. The method according to claim 10, wherein the polysaccharide is inulin, pectin, sodium alginate or agar, or wherein the polypeptide is casein or gelatin.

12. The method according to claim 1, wherein the pharmacologically inactive water-soluble polymer is a synthetic polymer.

13. The method according to claim 12, wherein the synthetic polymer is a polyvinyl polymer or a copolymer of acrylic acid.

14. The method according to claim 13, wherein the polyvinyl polymer is polyvinyl alcohol, polyvinylpyrrolidone or polystyrene sulfonate.

15. The method according to claim 14, wherein the polyvinyl polymer is polyvinylpyrrolidone.

16. The method according to claim 1, wherein the active ingredient is a carbonic anhydrase inhibitor, a β-adrenergic blocking agent, an ACE inhibitor, an antiviral, a tetracycline antibiotic, a macrolide antibiotic or a retinoid.

17. The method according to claim 16, wherein the active ingredient is acetazolamide, chlorzolamide, ethoxzolamide, methazolamide, timolol, atenolol, enalaprilic acid, enalaprilic acid ethyl ester, captopril, lisinopril, acyclovir, trifluridine, zidovudine, vidarabine, virazole, tetracycline, chlortetracycline, oxytetracycline, demeclocycline, methacycline, doxycycline, minocycline, erythromycin, josamycin, rosamicin, tylosin, troleandomycin, spiramycin, Vitamin A, Vitamin A-acetate, retinal, retinoic acid, isotretinoin, etretinate, acitretin or β-carotene.

18. The method according to claim 1, wherein the active ingredient is a steroid.

19. The method according to claim 18, wherein the steroid is an androgen, estrogen, progestin, diuretic, anabolic agent, anesthetic or glucocorticoid.

20. The method according to claim 19, wherein the steroid is hydrocortisone, dexamethasone, prednisolone, 17β-estradiol, 17α-ethinylestradiol, ethinylestradiol 3-methyl ether, estriol, norethindrone, norethindrone acetate, norgestrel, ethisterone, methoxyprogesterone acetate, progesterone, 17-methyltestosterone, triamcinolone, testosterone, spironolactone or alfaxalone.

21. The method according to claim 1, wherein the active ingredient is carbamazepine, phenytoin, ketoconazole, itraconazole, metronidazole benzoate, flubendazole, co-trimoxazole, miconazole, carmustine, chlorambucil, doxorubicin, lomustine, melphalan, methotrexate, dicumarol, nitroglycerin, flunarizine, alprostadil, prostacyclin, digitoxin, digoxin, aspirin, apomorphine, famotidine, furosemide, flurbiprofen, ibuprofen, indomethacin, piroxicam, lidocaine, sulindac, pentobarbital, phenobarbital, secobarbital, chlordiazepoxide, diazepam, medazepam, oxazepam or lorazepam.

22. The method according to claim 1, wherein the active ingredient is the reduced, biooxidizable, blood-brain barrier penetrating, lipoidal dihydropyridine form of a dihydropyridine ⇌ pyridinium salt redox system for brain-targeted drug delivery.

23. The method according to claim 22, wherein the dihydropyridine form is a compound of the formula

[D-DHC]

wherein [D] is a centrally acting drug species and [DHC] is the reduced, biooxidizable, blood-brain barrier penetrating, lipoidal form of a dihydropyridine ⇌ pyriclinium salt redox carrier.

24. The method according to claim 23, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

25. The method according to claim 1, wherein the cyclodextrin comprises at least one member selected from the group consisting of γ-cyclodextrin, β-cyclodextrin, α-cyclodextrin, hydroxypropyl-β-cyclodextrin, hydroxypropyl-γ-cyclodextrin, glucosyl-β-cyclodextrin, glucosyl-γ-cyclodextrin, maltosyl-β-cyclodextrin and maltosyl-γ-cyclodextrin, the polymer is hydroxypropyl methylcellulose, sodium carboxymethylcellulose or polyvinylpyrrolidone and the active ingredient is a carbonic anhydrase inhibitor, a steroid, an ACE inhibitor, a tetracycline antibiotic, a macrolide antibiotic, an antiviral or a retinoid.

26. A method for solubilizing and/or stabilizing a lipophilic and/or water-labile active ingredient which is a drug, cosmetic additive, food additive or agrochemical, in an aqueous medium, said method comprising complexing said active ingredient in an aqueous medium comprising from about 0.1 to about 70% (weight/volume) of cyclodextrin and from about 0.001 to about 5% (weight/volume) of a pharmacologically inactive water-soluble polymer acceptable for use in a pharmaceutical, cosmetic, food or agricultural composition, the polymer and cyclodextrin being dissolved in the aqueous medium before the active ingredient is added, the aqueous medium which comprises the polymer and cyclodextrin being maintained at from about 30° to about 150° C. for a period of from about 0.1 to about 100 hours before, during and/or after the active ingredient is added.

27. The method according to claim 26, wherein the aqueous medium is maintained at from about 30° to about 150° C. for from about 0.1 to about 100 hours before the active ingredient is added.

28. The method according to claim 26, wherein the aqueous medium is maintained at from about 30° to about 150° C. for from about 0.1 to about 100 hours after the active ingredient is added.

29. The method according to claim 26, wherein the amount of water-soluble polymer is from about 0.01 to about 0.5% (weight/volume).

30. The method according to claim 26, wherein the cyclodextrin comprises at least one member selected from the group consisting of α-,β- and γ-cyclodextrin and the hydroxypropyl, hydroxyethyl, dihydroxypropyl, glucosyl and maltosyl derivatives of α- β- and γ-cyclodextrin having molar degree of substitution of from about 0.05 to about 10.

31. The method according to claim 26, wherein the pharmacologically inactive water-soluble polymer is a cellulose derivative.

32. The method according to claim 31, wherein the cellulose derivative is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethylcellulose or sodium carboxymethylcellulose.

33. The method according to claim 32, wherein the cellulose derivative is hydroxypropyl methylcellulose.

34. The method according to claim 32, wherein the cellulose derivative is sodium carboxymethylcellulose.

35. The method according to claim 26, wherein the pharmacologically inactive water-soluble polymer is a natural polysaccharide or polypeptide.

36. The method according to claim 35, wherein the polysaccharide is inulin, pectin, sodium alginate or agar, or wherein the polypeptide is casein or gelatin.

37. The method according to claim 26, wherein the pharmacologically inactive water-soluble polymer is a synthetic polymer.

38. The method according to claim 37, wherein the synthetic polymer is a polyvinyl polymer or a copolymer of acrylic acid.

39. The method according to claim 38, wherein the polyvinyl polymer is polyvinyl alcohol, polyvinylpyrrolidone or polystyrene sulfonate.

40. The method according to claim 39, wherein the polyvinyl polymer is polyvinylpyrrolidone.

41. The method according to claim 26, wherein the active ingredient is a carbonic anhydrase inhibitor, a β-adrenergic blocking agent, an ACE inhibitor, an antiviral, a tetracycline antibiotic, a macrolide antibiotic or a retinoid.

42. The method according to claim 41, wherein the active ingredient is acetazolamide, chlorzolamide, ethoxzolamide, methazolamide, timolol, atenolol, enalaprilic acid, enalaprilic acid ethyl ester, captopril, lisinopril, acyclovir, trifluridine, zidovudine, vidarabine, virazole, tetracycline, chlortetracycline, oxytetracycline, demeclocycline, methacycline, doxycycline, minocycline, erythromycin, josamycin, rosamicin, tylosin, troleandomycin, spiramycin, Vitamin A, Vitamin A-acetate, retinal, retinoic acid, isotretinoin, etretinate, acitretin or β-carotene.

43. The method according to claim 26, wherein the active ingredient is a steroid.

44. The method according to claim 43, wherein the steroid is an androgen, estrogen, progestin, diuretic, anabolic agent, anesthetic or glucocorticoid.

45. The method according to claim 44, wherein the steroid is hydrocortisone, dexamethasone, prednisolone, 17β-estradiol, 17α-ethinylestradiol, ethinylestradiol 3-methyl ether, estriol, norethindrone, norethindrone acetate, norgestrel, ethisterone, methoxyprogesterone acetate, progesterone, 17-methyltestosterone, triamcinolone, testosterone, spironolactone or alfaxalone.

46. The method according to claim 26, wherein the active ingredient is carbamazepine, phenytoin, ketoconazole, itraconazole, metronidazole benzoate, fiubendazole, co-trimoxazole, miconazole, carmustine, chlorambucil, doxorubicin, lomustine, melphalan, methotrexate, dicumarol, nitroglycerin, fiunarizine, alprostadil, prostacyclin, digitoxin, digoxin, aspirin, apomorphine, famotidine, furosemide, fiurbiprofen, ibuprofen, indomethacin, piroxicam, lidocaine, sulindac, pentobarbital, phenobarbital, secobarbital, chlordiazepoxide, diazepam, medazepam, oxazepam or lorazepam.

47. The method according to claim 26, wherein the active ingredient is the reduced, biooxidizable, blood-brain barrier penetrating, lipoidal dihydropyridine form of a dihydropyridine ⇌ pyridinium salt redox system for brain-targeted drug delivery.

48. The method according to claim 47, wherein the dihydropyridine form is a compound of the formula

[D-DHC]

wherein [D] is a centrally acting drug species and [DHC] is the reduced, biooxidizable, blood-brain barrier penetrating, lipoidal form of a dihydropyridine ⇌ pyridinium salt redox carrier.

49. The method according to claim 48, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

50. The method according to claim 26, wherein the cyclodextrin comprises at least one member selected from the group consisting of γ-cyclodextrin, β-cyclodextrin, α-cyclodextrin, hydroxypropyl-β-cyclodextrin, hydroxypropyl-γ-cyclodextrin, glucosyl-β-cyclodextrin, glucosyl-γ-cyclodextrin, maltosyl-β-cyclodextrin and maltosyl-γ-cyclodextrin, the polymer is hydroxypropyl methylcellulose, sodium carboxymethylcellulose or polyvinylpyrrolidone and the active ingredient is a carbonic anhydrase inhibitor, an ACE inhibitor, a tetracycline antibiotic, a macrolide antibiotic, an antiviral or a retinoid.

51. A co-complex of a lipophilic and/or water-labile active ingredient which is a drug, cosmetic additive, food additive or agrochemical with a cyclodextrin and a pharmacologically inactive water-soluble polymer acceptable for use in a pharmaceutical, cosmetic, food or agricultural composition, the ratio by weight of cyclodextrin to polymer being from about 4:1 to about 50,000:1, the molecular ratio of active ingredient to cyclodextrin being from about 0.33 to about 3.0 molecules of active ingredient per molecule of cyclodextrin in the co-complex.

52. The co-complex according to claim 51, wherein the ratio by weight of cyclodextrin to polymer is from about 4:1 to about 10,000:1.

53. The co-complex according to claim 52, wherein the ratio by weight of cyclodextrin to polymer is from about 100:1 to about 1,000:1.

54. The co-complex according to claim 51, wherein the cyclodextrin comprises at least one member selected from the group consisting of α-, β - and γ-cyclodextrin and the hydroxypropyl, hydroxyethyl, dihydroxypropyl, glucosyl and maltosyl derivatives of α-, β- and γ-cyclodextrin having a molar degree of substitution of from about 0.05 to about 10.

55. The co-complex according to claim 51, wherein the pharmacologically inactive water-soluble polymer is a cellulose derivative.

56. The co-complex according to claim 55, wherein the cellulose derivative is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethylcellulose or sodium carboxymethylcellulose.

57. The co-complex according to claim 51, wherein the pharmacologically inactive water-soluble polymer is a natural polysaccharide or polypeptide.

58. The co-complex according to claim 57, wherein the polysaccharide is inulin, pectin, sodium alginate or agar, or wherein the polypeptide is casein or gelatin.

59. The co-complex according to claim 51, wherein the pharmacologically inactive water-soluble polymer is a synthetic polymer.

60. The co-complex according to claim 59, wherein the synthetic polymer is a polyvinyl polymer or a copolymer of acrylic acid.

61. The co-complex according to claim 60, wherein the polyvinyl polymer is polyvinyl alcohol, polyvinylpyrrolidone or polystyrene sulfonate.

62. The co-complex according to claim 51, wherein the pharmacologically inactive water-soluble polymer is hydroxypropyl methylcellulose, sodium carboxymethylcellulose or polyvinylpyrrolidone.

63. The co-complex according to claim 51, wherein the active ingredient is a carbonic anhydrase inhibitor, a β-adrenergic blocking agent, an ACE inhibitor, an antiviral, a tetracycline antibiotic, a macrolide antibiotic or a retinoid.

64. The co-complex according to claim 51, wherein the active ingredient is a steroid.

65. The co-complex according to claim 64, wherein the steroid is an androgen, estrogen, progestin, diuretic, anabolic agent, anesthetic or glucocorticoid.

66. The co-complex according to claim 63, wherein the active ingredient is acetazolamide, chlorzolamide, ethoxzolamide, methazolamide, timolol, atenolol, enalaprilic acid, enalaprilic acid ethyl ester, captopril, lisinopril, acyclovir, trifluridine, zidovudine, vidarabine, virazole, tetracycline, chlortetracycline, oxytetracycline, demeclocycline, methacycline, doxycycline, minocycline, erythromycin, josamycin, rosamicin, tylosin, troleandomycin, spiramycin, Vitamin A, Vitamin A-acetate, retinal, retinoic acid, isotretinoin, etretinate, acitretin or β-carotene.

67. The co-complex according to claim 51, wherein the active ingredient is carbamazepine, phenytoin, ketoconazole, itraconazole, metronidazole benzoate, flubendazole, co-trimoxazole, miconazole, carmustine, chlorambucil, doxorubicin, lomustine, melphalan, methotrexate, dicumarol, nitroglycerin, flunarizine, alprostadil, prostacyclin, digitoxin, digoxin, aspirin, apomorphine, famotidine, furosemide, flurbiprofen, ibuprofen, indomethacin, piroxicam, lidocaine, sulindac, pentobarbital, phenobarbital, secobarbital, chlordiazepoxide, diazepam, medazepam, oxazepam or lorazepam.

68. The co-complex according to claim 65, wherein the steroid is hydrocortisone, dexamethasone, prednisolone, 17β-estradiol, 17α-ethinylestradiol, ethinylestradiol 3-methyl ether, estriol, norethindrone, norethindrone acetate, norgestrel, ethisterone, methoxyprogesterone acetate, progesterone, 17-methyltestosterone, triamcinolone, testosterone, spironolactone or alfaxalone.

69. The co-complex according to claim 51, wherein the active ingredient is the reduced, biooxidizable, blood-brain barrier penetrating, lipoidal dihydropyridine form of a dihydropyridine ⇌ pyridinium salt redox system for brain-targeted drug delivery.

70. The co-complex according to claim 69, wherein the dihydropyridine form is a compound of the formula

[D-DHC]

wherein [D] is a centrally acting drug species and [DHC] is the reduced, biooxidizable, blood-brain barrier penetrating, lipoidal form of a dihydropyridine ⇌ pyridinium salt redox carrier.

71. The co-complex according to claim 70, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

72. The co-complex according to claim 51, wherein the cyclodextrin comprises at least one member selected from the group consisting of γ-cyclodextrin, β-cyclodextrin, α-cyclodextrin, hydroxypropyl-β -cyclodextrin, hydroxypropyl-γ- cyclodextrin, glucosyl-β-cyclodextrin, glucosyl-γ-cyclodextrin, maltosyl-β-cyclodextrin and maltosyl-γ-cyclodextrin, the polymer is hydroxypropyl methylcellulose, sodium carboxymethylcellulose or polyvinylpyrrolidone and the active ingredient is a carbonic anhydrase inhibitor, a steroid, an ACE inhibitor, a tetracycline antibiotic, a macrolide antibiotic, an antiviral or a retinoid.

73. A composition comprising:
(a) a complex prepared by complexing a lipophilic and/or water-labile active ingredient which is a drug, cosmetic additive, food additive or agochemical in an aqueous medium comprising from about 0.1 to about 70% (weight/volume) of cyclodextrin and from about 0.001 to about 5% (weight/volume) of a pharmacologically inactive water-soluble polymer acceptable for use in a pharmaceutical, cosmetic, food or agricultural composition, the polymer and cyclodextrin being dissolved in the aqueous medium before the active ingredient is added, the aqueous medium which comprises the polymer and cyclodextrin being maintained at from about 30° to about 150° C. for a period of from about 0.1 to about 100 hours before, during and/or after the active ingredient is added, optionally followed by removal of water; and (b) a non-toxic carrier therefor acceptable for use in a pharmaceutical, cosmetic, food or agricultural composition.

74. The composition according to claim 73, wherein the cyclodextrin comprises at least one member selected from the group consisting of α-, β- and γ-cyclodextrin and the hydroxypropyl, hydroxyethyl, dihydroxypropyl, glucosyl and maltosyl derivatives of α-, β - and γ-cyclodextrin having a molar degree of substitution of from about 0.05 to about 10.

75. The composition according to claim 73, wherein the pharmacologically inactive water-soluble polymer is a cellulose derivative.

76. The composition according to claim 75, wherein the cellulose derivative is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethylcellulose or sodium carboxymethylcellulose.

77. The composition according to claim 73, wherein the pharmacologically inactive water-soluble polymer is a natural polysaccharide or polypeptide.

78. The composition according to claim 77, wherein the polysaccharide is inulin, pectin, sodium alginate or agar, or wherein the polypeptide is casein or gelatin.

79. The composition method according to claim 73, wherein the pharmacologically inactive water-soluble polymer is a synthetic polymer.

80. The composition according to claim 79, wherein the synthetic polymer is a polyvinyl polymer or a copolymer of acrylic acid.

81. The composition according to claim 80, wherein the polyvinyl polymer is polyvinyl alcohol, polyvinylpyrrolidone or polystyrene sulfonate.

82. The composition according to claim 73, wherein the pharmacologically inactive water-soluble polymer is hydroxypropyl methylcelluclose, sodium carboxymethylcellulose or polyvinylpyrrolidone.

83. The composition according to claim 73, wherein the amount of water-soluble polymer is from about 0.01 to about 0.5% (weight/volume).

84. The composition according to claim 73, wherein the active ingredient is a carbonic anhydrase inhibitor, a β-adrenergic blocking agent, an ACE inhibitor, an antiviral, a tetracycline antibiotic, a macrolide antibiotic or a retinoid.

85. The composition according to claim 73, wherein the active ingredient is a steroid.

86. The composition according to claim 85, wherein the steroid is an androgen, estrogen, progestin, diuretic, anabolic agent, anesthetic or glucocorticoid.

87. The composition according to claim 73, wherein the active ingredient is acetazolamide, chlorzolamide, ethoxzolamide, methazolamide, timolol, atenolol, enalaprilic acid, enalaprilic acid ethyl ester, captopril, lisinopril, acyclovir, trifluridine, zidovudine, vidarabine, virazole, tetracycline, chlortetracycline, oxytetracycline, demeclocycline, methacycline, doxycycline, minocycline, erythromycin, josamycin, rosamicin, tylosin, troleandomycin, spiramycin, Vitamin A, Vitamin A-acetate, retinal, retinoic acid, isotretinoin, etretinate, acitretin or β-carotene.

88. The composition according to claim 73, wherein the active ingredient is carbamazepine, phenytoin, ketoconazole, itraconazole, metronidazole benzoate, flubendazole, co-trimoxazole, miconazole, carmustine, chlorambucil, doxorubicin, lomustine, melphalan, methotrexate, dicumarol, nitroglycerin, flunarizine, alprostadil, prostacyclin, digitoxin, digoxin, aspirin, apomorphine, famotidine, furosemide, flurbiprofen, ibuprofen, indomethacin, piroxicam, lidocaine, sulindac, pentobarbital, phenobarbital, secobarbital, chlordiazepoxide, diazepam, medazepam, oxazepam or lorazepam.

89. The composition according to claim 86, wherein the steroid is hydrocortisone, dexamethasone, prednisolone, 17β-estradiol, 17α-ethinylestradiol, ethinylestradiol 3-methyl ether, estriol, norethindrone, norethindrone acetate, norgestrel, ethisterone, methoxyprogesterone acetate, progesterone, 17-methyltestosterone, triamcinolone, testosterone, spironolactone or alfaxalone.

90. The composition according to claim 73, wherein the active ingredient is the reduced, biooxidizable, blood-brain barrier penetrating, lipoidal dihydropyridine form of a dihydropyridine ⇌ pyridinium salt redox system for brain-targeted drug delivery.

91. The composition according to claim 90, wherein the dihydropyridine form is a compound of the formula

[D-DHC]

wherein [D] is a centrally acting drug species and [DHC] is the reduced, biooxidizable, blood-brain barrier penetrating, lipoidal form of a dihydropyridine ⇌ pyridinium salt redox carrier.

92. The composition according to claim 91, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptatnine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

93. The composition according to claim 73, wherein the cyclodextrin comprises at least one member selected from the group consisting of γ-cyclodextrin, β-cyclodextrin, α-cyclodextrin, hydroxypropyl-β-cyclodextrin, hydroxypropyl-γ-cyclodextrin, glucosyl-β -cyclodextrin, glucosyl-γ-cyclodextrin, maltosyl-β-cyclodextrin and maltosyl-γ-cyclodextrin, the polymer is hydroxypropyl methylcellulose, sodium carboxymethylcellulose or polyvinylpyrrolidone and the active ingredient is a carbonic anhydrase inhibitor, a steroid, an ACE inhibitor, a tetracycline antibiotic, a macrolide antibiotic, an antiviral or a retinoid.

94. The composition according to claim 73, wherein all ingredients are ophthalmically acceptable, and wherein the active ingredient is a carbonic anhydrase inhibitor, a steroid, an ACE inhibitor, a β-blocker, an antiviral or an antibiotic, the polymer is hydroxypropyl methylcellulose or polyvinylpyrrolidone, and the cyclodextrin comprises at least one member selected from the group consisting of γ-cyclodextrin, β-cyclodextrin, α-cyclodextrin, hydroxypropyl-β-cyclodextrin, hydroxypropyl-γ -cyclodextrin, glucosyl-β-cyclodextrin, glucosyl-γ-cyclodextrin, maltosyl-β -cyclodextrin and maltosyl-γ-cyclodextrin.

95. The composition according to claim 73, wherein all ingredients are acceptable for use in a mouthwash, and wherein the active ingredient is a steroid, an antifungal, an antiviral or an antiseptic, the polymer is hydroxypropyl methylcellulose, sodium carboxymethylcellulose or polyvinylpyrrolidone, and the cyclodextrin comprises at least one member selected from the group consisting of γ-cyclodextrin, β-cyclodextrin, α-cyclodextrin, hydroxypropyl-β-cyclodextrin, hydroxypropyl-γ-cyclodextrin, glucosyl-β-cyclodextrin, glucosyl-γ-cyclodextrin, maltosyl-β-cyclodextrin and maltosyl-γ-cyclodextrin.

96. A composition comprising:
(a) a co-complex of a lipophilic and/or water-labile active ingredient which is a drug, cosmetic additive, food additive or agrochemical with a cyclodextrin and a pharmacologically inactive water-soluble polymer acceptable for use in a pharmaceutical, cosmetic, food or agricultural composition, the ratio by weight of cyclodextrin to polymer being from about 4:1 to about 50,000:1, the molecular ratio of active ingredient to cyclodextrin being from about 0.33 to about 3.0 molecules of active ingredient per molecule of cyclodextrin in the co-complex; and
(b) a non-toxic carrier therefor acceptable for use in a pharmaceutical, cosmetic, food or agricultural composition.

97. The composition according to claim 96, wherein the ratio by weight of cyclodextrin to polymer is from about 4:1 to about 10,000:1.

98. The composition according to claim 97, wherein the ratio by weight of cyclodextrin to polymer is from about 100:1 to about 1,000:1.

99. The composition according to claim 96, wherein the cyclodextrin comprises at least one member selected from the group consisting of α-, β- and γ-cyclodextrin and the hydroxypropyl, hydroxyethyl, dihydroxypropyl, glucosyl and maltosyl derivatives of α-, β- and γ-cyclodextrin having a molar degree of substitution of from about 0.05 to about 10.

100. The composition according to claim 96, wherein the pharmacologically inactive water-soluble polymer is a cellulose derivative.

101. The composition according to claim 100, wherein the cellulose derivative is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethylcellulose or sodium carboxymethylcellulose.

102. The composition according to claim 96, wherein the pharmacologically inactive water-soluble polymer is a natural polysaccharide or polypeptide.

103. The composition according to claim 102, wherein the polysaccharide is inulin, pectin, sodium alginate or agar, or wherein the polypeptide is casein or gelatin.

104. The composition according to claim 96, wherein the pharmacologically inactive water-soluble polymer is a synthetic polymer.

105. The composition according to claim 104, wherein the synthetic polymer is a polyvinyl polymer or a copolymer of acrylic acid.

106. The composition according to claim 105, wherein the polyvinyl polymer is polyvinyl alcohol, polyvinylpyrrolidone or polystyrene sulfonate.

107. The composition according to claim 96, wherein the pharmacologically inactive water-soluble polymer is hydroxypropyl methylcellulose, sodium carboxymethylcellulose or polyvinylpyrrolidone.

108. The composition according to claim 96, wherein the active ingredient is a carbonic anhydrase inhibitor, a β-adrenergic blocking agent, an ACE inhibitor, an antiviral, a tetracycline antibiotic, a macrolide antibiotic or a retinoid.

109. The composition according to claim 96, wherein the active ingredient is a steroid.

110. The composition according to claim 109, wherein the steroid is an androgen, estrogen, progestin, diuretic, anabolic agent, anesthetic or glucocorticoid.

111. The composition according to claim 96, wherein the active ingredient is acetazolamide, chlorzolamide, ethoxzolamide, methazolamide, timolol, atenolol, enalaprilic acid, enalaprilic acid ethyl ester, captopril, lisinopril, acyclovir, trifluridine, zidovudine, vidarabine, virazole, tetracycline, chlonetracycline, oxytetracycline, demeclocycline, methacycline, doxycycline, minocycline, erythromycin, josamycin, rosamicin, tylosin, troleandomycin, spiramycin, Vitamin A, Vitamin A-acetate, retinal, retinoic acid, isotretinoin, etretinate, acitretin or β-carotene.

112. The composition according to claim 96, wherein the active ingredient is carbatnazepine, phenytoin, ketoconazole, itraconazole, metronidazole benzoate, flubendazole, co-trimoxazole, miconazole, carmustine, chlorambucil, doxorubicin, lomustine, melphalan, methotrexate, dicumarol, nitroglycerin, flunarizine, alprostadil, prostacyclin, digitoxin, digoxin, aspirin, apomorphine, famotidine, furosemide, flurbiprofen, ibuprofen, indomethacin, piroxicam, lidocaine, sulindac, pentobarbital, phenobarbital, secobarbital, chlordiazepoxide, diazepam, medazepam, oxazepam or lorazepam.

113. The composition according to claim 110, wherein the steroid is hydrocortisone, dexamethasone, prednisolone, 17β-estradiol, 17α-ethinylestradiol, ethinylestradiol 3-methyl ether, estriol, norethindrone, norethindrone acetate, norgestrel, ethisterone, methoxyprogesterone acetate, progesterone, 17-methyltestosterone, triamcinolone, testosterone, spironolactone or alfaxalone.

114. The composition according to claim 96, wherein the active ingredient is the reduced, biooxidizable, blood-brain barrier penetrating, lipoidal dihydropyridine form of a dihydropyridine ⇌ pyridinium salt redox system for brain-targeted drug delivery.

115. The composition according to claim 114, wherein the dihydropyridine form is a compound of the formula

[D-DHC]

wherein [D] is a centrally acting drug species and [DHC] is the reduced, biooxidizable, blood-brain barrier penetrating, lipoidal form of a dihydropyridine ⇌ pyridinium salt redox carrier.

116. The composition according to claim 115, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

117. The composition according to claim 96, wherein the cyclodextrin comprises at least one member selected from the group consisting of γ-cyclodextrin, β-cyclodextrin, α-cyclodextrin, hydroxypropyl-β-cyclodextrin, hydroxypropyl-γ-cyclodextrin, glucosyl-β-cyclodextrin, glucosyl-γ-cyclodextrin, maltosyl-β-cyclodextrin and maltosyl-γ-cyclodextrin, the polymer is hydroxypropyl methylcellulose, sodium carboxymethylcellulose or polyvinylpyrrolidone and the active ingredient is a carbonic anhydrase inhibitor, a steroid, an ACE inhibitor, a tetracycline antibiotic, a macrolide antibiotic, an antiviral or a retinoid.

118. The composition according to claim 96, wherein all ingredients are ophthalmically acceptable, and wherein the active ingredient is a carbonic anhydrase inhibitor, a steroid, an ACE inhibitor, a β-blocker, an antiviral or an antibiotic, the polymer is hydroxypropyl methylcellulose or polyvinylpyrrolidone, and the cyclodextrin comprises at least one member selected from the group consisting of γ-cyclodextrin, hydroxypropyl-β -cyclodextrin, hydroxypropyl-γ-cyclodextrin, glucosyl-β-cyclodextrin, glucosyl-γ-cyclodextrin, maltosyl-β-cyclodextrin and maltosyl-γ -cyclodextrin.

119. The composition according to claim 96, wherein all ingredients are acceptable for use in a mouthwash, and wherein the active ingredient is a steroid, an antifungal, an antiviral or an antiseptic, the polymer is hydroxypropyl methylcellulose, sodium carboxymethylcellulose or polyvinylpyrrolidone, and the cyclodextrin comprises at least one member selected from the group consisting of γ-cyclodextrin, β-cyclodextrin, α-cyclodextrin, hydroxypropyl-β-cyclodextrin, hydroxypropyl-γ -cyclodextrin, glucosyl-β-cyclodextrin, glucosyl-γ-cyclodextrin, maltosyl-β -cyclodextrin and maltosyl-γ-cyclodextrin.

* * * * *

UNITED STATES PATENT AND TRADEMARK OFFICE
CERTIFICATE OF CORRECTION

PATENT NO. : 5,472,954
DATED : December 5, 1995
INVENTOR(S) : Thorsteinn LOFTSSON It is certified that error appears in the above-indentified patent and that said Letters Patent is hereby corrected as shown below:

On the title page, line 7, under the item [73] [*] Notice:", delete "The portion of the term of this patent subsequent to Jun. 28, 2011, has been disclaimed." and insert in its stead: --The term of this patent shall not extend beyond the expiration date of Patent No. 5,324,718.--

Signed and Sealed this

Sixteenth Day of July, 1996

Attest:

BRUCE LEHMAN

*Attesting Officer*                *Commissioner of Patents and Trademarks*